US010676708B2

(12) United States Patent
Chung et al.

(10) Patent No.: US 10,676,708 B2
(45) Date of Patent: Jun. 9, 2020

(54) METHOD FOR PREPARING MICROBIAL PREPARATION AND MICROBIAL PREPARATION PRODUCED BY THE SAME

(71) Applicant: RNA INC., Gyeonggi-do (KR)

(72) Inventors: Dae Kyun Chung, Gyeonggi-do (KR); Hangeun Kim, Gyeonggi-do (KR); Seung Su Lee, Gyeonggi-do (KR); Bong Jun Jung, Gyeonggi-do (KR); Hye Rim Kim, Daegu (KR); Yoon Doo Lee, Gyeonggi-do (KR); Jae Yeon Park, Gyeonggi-do (KR); Boram Jeon, Gyeonggi-do (KR); Seong Jae Kim, Gyeonggi-do (KR)

(73) Assignee: RNA INC., Gyeonggi-Do (KR)

( * ) Notice: Subject to any disclaimer, the term of this patent is extended or adjusted under 35 U.S.C. 154(b) by 378 days.

(21) Appl. No.: 15/515,918

(22) PCT Filed: Sep. 30, 2015

(86) PCT No.: PCT/KR2015/010325
§ 371 (c)(1),
(2) Date: Mar. 30, 2017

(87) PCT Pub. No.: WO2016/053003
PCT Pub. Date: Apr. 7, 2016

(65) Prior Publication Data
US 2017/0306289 A1 Oct. 26, 2017

(30) Foreign Application Priority Data
Sep. 30, 2014 (KR) .................. 10-2014-0131390

(51) Int. Cl.
| C12N 1/20 | (2006.01) |
| C12P 23/00 | (2006.01) |
| C12P 1/04 | (2006.01) |
| A23L 19/00 | (2016.01) |
| A23L 33/135 | (2016.01) |
| A23L 11/00 | (2016.01) |
| A23C 9/123 | (2006.01) |
| A23G 3/36 | (2006.01) |
| A61K 8/99 | (2017.01) |
| A61Q 19/00 | (2006.01) |
| A61Q 19/08 | (2006.01) |
| C12N 9/42 | (2006.01) |
| C12R 1/225 | (2006.01) |
| C12R 1/25 | (2006.01) |

(52) U.S. Cl.
CPC ............. *C12N 1/20* (2013.01); *A23C 9/1234* (2013.01); *A23G 3/366* (2013.01); *A23L 11/07* (2016.08); *A23L 19/09* (2016.08); *A23L 33/135* (2016.08); *A61K 8/99* (2013.01); *A61Q 19/00* (2013.01); *A61Q 19/007* (2013.01); *A61Q 19/08* (2013.01); *C12N 9/2445* (2013.01); *C12P 1/04* (2013.01); *C12P 23/00* (2013.01); *C12Y 302/01021* (2013.01); *A23V 2002/00* (2013.01); *A23Y 2220/67* (2013.01); *A61K 2800/70* (2013.01); *A61K 2800/85* (2013.01); *C12R 1/225* (2013.01); *C12R 1/25* (2013.01)

(58) Field of Classification Search
None
See application file for complete search history.

(56) References Cited

U.S. PATENT DOCUMENTS

2001/2008893    4/2012    Kamo et al.

FOREIGN PATENT DOCUMENTS

| EP | 2570132 A2 | 3/2013 |
| JP | 2004000167 A | 1/2004 |
| JP | 2004000168 A | 1/2004 |
| JP | 2010029119 A | 2/2010 |
| JP | 2010029119 A1 | 2/2010 |
| JP | 2011229476 A | 11/2011 |
| KR | 10-2003-0071396 A | 9/2003 |
| KR | 10-0613764 B1 | 8/2006 |
| KR | 1020070078107 A | 7/2007 |
| KR | 100832344 B1 | 5/2008 |
| KR | 10-2008-0102773 A | 11/2008 |
| KR | 10-2010-0035786 A | 4/2010 |
| KR | 1020110078678 A | 7/2011 |
| KR | 1020140006683 A | 1/2014 |
| KR | 20140043513 A | 4/2014 |
| KR | 1020140043421 A1 | 4/2014 |
| KR | 1020140063948 A | 5/2014 |
| KR | 101406975 B | 6/2014 |
| KR | 1020140099104 A | 8/2014 |

(Continued)

OTHER PUBLICATIONS

KR20030071396A English translation (English translation referred to provided by KIPO). (Year: 2003).*
Kim, et al., J. Microbiol. Biotechnol. 25:74, Supplemental Data. (Year: 2015).*
Hyun, C., et al., "Differential Transformation of Gensenosides from Panax ginsent by Lactic Acid Bacteria", "Journal of Microbiology and Biotechnology", 2006, pp. 1628-1633, vol. 16, No. 10, Publisher: The Korean Society for Microbiology and Biotechnology.
Park, R.H., et al., "-Glycosidase-Assisted Bioconversion of Gensenosides in Purified Crude Saponin and Extracts from Red Ginseng (*Panax ginseng* C.A. Meyer)", "Food Sci. Biotechnol.", 2013, pp. 1629-1638, vol. 22, No. 6, Publisher: Springer.

(Continued)

*Primary Examiner* — Michael Barker
(74) *Attorney, Agent, or Firm* — Hultquist, PLLC; Steven J. Hultquist

(57) ABSTRACT

The present disclosure relates to a method for preparing an aglycone or hydrolyzed glycoside converted from a glycoside and, specifically, to a method for preparing an aglycone or hydrolyzed glycoside from a glycoside by converting a glycoside into an aglycone form or hydrolyzed glycoside by using a microorganism producing β-glycosidase, and then recovering the aglycone or hydrolyzed glycoside accumulated in the cells of the microorganism.

10 Claims, 9 Drawing Sheets
(8 of 9 Drawing Sheet(s) Filed in Color)

(56) References Cited

FOREIGN PATENT DOCUMENTS

KR             101440469 B      9/2014
WO     WO2006118364 A1    11/2006

OTHER PUBLICATIONS

Thuan, N., et al., "Recent biotechnological progress in enzymatic synthesis of glycosides", "J. Ind. Microbiiol Biotechnol", 2013, pp. 1329-1356, vol. 40, No. DOI 10.1007/s10295-0, Publisher: Society for Industrial Microbiology and Biotechnology; Springer.

Kim, B., et al., "Changes of Ginsenosides in Korean Red Ginseng (*Panax ginseng*) Fermented by Lactobacillus Plantarum M1", "Process Biochemistry", 2010, pp. 1319-1324, vol. 45.

Lee, B., et al., "Transformation of the Glycosides From Food Materials by Probiotics and Food Microorganisms", "J. Microbiol. Biotechol.", 2006, pp. 497-504, vol. 16, No. 4.

Ali, A.A., et al., "Effects of soybean isoflavones, probiotics, and their interactions on lipid metabolism and endocrine system in an animal model of obesity and diabetes", "Journal of Nutritional Biochemistry", Apr. 22, 2004, pp. 583-590, vol. 15.

Cavallini, D.C.U., et al., "Isoflavones Supplementation of a Probiotic Fermented Soy Product: Effects on Quality Characteristics and Isoflavones Profile", "Alimentos e Nutrio Araraquara", Apr.-Jun. 2010, pp. 175-182, vol. 21, No. 2.

Kim, H., et al., "Effects of Oral Intake of Kimchi-Derived Lactobacillus plantarum K8 Lysates on Skin Moisturizing", "Journal of Microbiology and Biotechnology", Sep. 1, 2014, pp. 74-80, vol. 25, No. 1.

Kuo, L-C., et al., "Hydrolysis of black soybean isoflavone glycosides by Bacillus subtilis natto", "Applied Microbiology and Biotechnology", May 20, 2006, pp. 314-320, vol. 73.

Lee, S-H., et al., "Deglycosylation of Isoflavones in Iso!avone-Rich Soy Germ Flour by Aspergillus oryzae KACC 40247", "Journal of Agricultural and Food Chemistry", Nov. 12, 2013, pp. 12101-12110, vol. 61.

New Hope Network, "Probiotics Boost Soy Milk Isoflavones", Dec. 10, 2007, pp. http://www.newhope.com/node/156.

Jung, H., et al., "*Lactobacillus ginsenosidimutans* sp. nov., Isolated from Kimchi with the Ability to Transform Ginsenosides", "Antonie van Leeusenhoek", 2013, p. 867-876, vol. 103.

Kim, S., et al., "Enzymatic Transformation of Ginsenoside Rb 1 by Lactobacillus Pentosus Strain 6105 from Kimchi", "Journal of Ginseng Research", 2012, p. 291-297, vol. 36, No. 3.

\* cited by examiner

FIG. 9

| test items | Results | | Test items | Results | | Test items | Results | |
|---|---|---|---|---|---|---|---|---|
| | 24 h | 48 h | | 24 h | 48 h | | 24 h | 48 h |
| Control | − | − | Inositol | − | − | D-melezitose | + | + |
| Glycerol | − | − | D-manitol | + | + | D-raffinose | − | − |
| Erythritol | − | − | D-sorbitol | + | + | Amidon | − | − |
| D-arabinose | − | − | MDM | − | − | Glycogen | − | − |
| L-arabinose | + | + | MDG | − | − | Xylitl | − | − |
| D-ribose | + | + | NAG | + | + | Gentiobiose | − | − |
| D-xylose | − | − | Amygdalin | − | ? | D-turanose | + | + |
| L-xylose | − | − | Arbutin | + | + | D-lyxose | − | − |
| D-adonitol | − | − | ESC | − | − | D-tagatose | − | − |
| MDX | − | − | Salicin | + | + | D-fucose | − | − |
| D-galactose | + | + | D-celobiose | − | − | L-fucose | − | − |
| D-glucose | + | + | D-maltose | + | + | D-arabitol | − | ? |
| D-fructose | + | + | D-lactose | + | + | L-arabitol | − | − |
| D-mannose | + | + | D-melibiose | − | + | GNT | + | + |
| DL-sorbose | − | − | D-saccharose | + | + | 2KG | − | − |
| L-rhamnose | − | − | D-trehalose | + | + | 5KG | − | ? |
| Dulcitol | − | − | Insulin | − | − | | | |

METHOD FOR PREPARING MICROBIAL PREPARATION AND MICROBIAL PREPARATION PRODUCED BY THE SAME

CROSS-REFERECE TO RELATED APPLICATIONS

This application is a U.S. national phase under the provisions of 35 U.S.C. § 371 of International Patent Application No. PCT/KR2015/010325 filed Sep. 30, 2015, which in turn claims priority of Korean Patent Application No. 10-2014-0131390 filed Sep. 30, 2014. The disclosures of such international patent application and Korean priority patent application are hereby incorporated herein by reference in their respective entireties, for all purposes.

TECHNICL FIELD

The present disclosure relates to a method for preparing a microbial preparation containing an aglycone or hydrolyzed glycoside in the cells and, specifically, to a method for preparing a microorganism which converting a glycoside into an aglycone form or hydrolyzed glycoside by using a microorganism producing β-glycosidase, and having the aglycone or hydrolyzed glycoside accumulated in the cells.

DESCRIPTION OF THE RELATED ART

Lactic acid bacteria are one of the most beneficial microorganisms available to humans and means a bacterial that decomposes carbohydrates such as glucose or lactose during fermentation to produce lactic acid. In 1858, the presence of lactic acid bacteria was discovered by the French microbiologist Louis Pasteur, and the Ilija Mecnikov, a Russian immunologist, was awarded the Nobel Prize for physiology in 1908, declared "the eternal youth hypothesis by the fermented milk" in his later years, and then claimed that the longevity cause of the Bulgarian people was in the lactic acid bacteria fermented milk, and from the claim, full-scale researches have begun and more than 300 kinds of lactic acid bacteria have been discovered so far. The lactic acid bacteria live in the intestines of the most mammals including the humans, and particularly, more than 100 trillion of 100 kinds of bacteria combining healthy and harmful bacteria are present in the intestines of the human body. Since the lactic acid bacteria produce the lactic acid as a metabolite to acidify the intestines, the lactic acid bacteria are known as bacteria which serve to inhibit proliferation of harmful bacteria and reduce the production of ammonia or carcinogens by abnormal fermentation, that is, performs the intestinal regulation.

It is known that the physiological activity of the lactic acid bacteria is that they mainly produce organic acids to lower the pH of the intestines, which inhibits the proliferation of harmful bacteria in the intestines and maintain the normal intestinal microbial flora. They also act to convert a glycoside isoflavone into an aglycone which is easily absorbed in the body by producing β-glucosidase.

Particularly, in the case of isoflavone, there are four forms of a glycoside to which sugar is coupled, an aglycone in which the sugar is removed, acetylglucoside, and malonylglucoside, and among them, the aglycone isoflavone is hydrolyzed by β-glucosidase in the intestines to be converted into an aglycone as an active aglycone and absorbed. However, isoflavone included in general foods is present as a glycoside form to which the sugar is coupled, and isoflavone taken from the diet needs to be converted into an aglycone form by the intestinal microorganism so as to be absorbed. Accordingly, the microorganism having activity of β-glycosidase may play a very important role in bioavailability of the isoflavone.

As a method of extracting isoflavone in the related art, there is a method of extracting powder of a plant including isoflavone with water, acidifying the extract, separating the extract from the sludge to pass through a column filled with an absorbent resin, absorbing isoflavone in the extract on the resin, passing an alcoholic solvent through the column, and recovering the isoflavone absorbed on the resin. As another method, there is a method of extracting isoflavone including a first step of binding and extracting isoflavone to cyclodextrin, a derivative thereof, or a polymer thereof by adding a plant or a plant processing product including isoflavone in the cyclodextrin, the derivative thereof, or the polymer thereof and a second step of isolating a binder of isoflavone and cyclodextrin from the extract by injecting a coagulant in the extract formed in the first step and the extraction. Particularly, in order to extract the aglycone isoflavone from the native beans, various mechanical and chemical methods are used, and there is a method of extracting isoflavone by using ultrasonic waves and then purifying the extract by liquid chromatography. However, the extraction method comprises many steps and includes problems such as a decrease in production rate, an increase in production cost, and possibility of contamination during a purifying process.

Bioconversion of glycoside isoflavone to aglycone isoflavone by microorganisms has been studied (Kuo et al., Appl Microbiol Biotechnol 2006.73:314-320; Lee et al., J Agric Food Chem 2013. 61:12101-12110), and above all, bioconversion of glycoside isoflavone to aglycone isoflavone by lactic acid bacteria is possible and researches therefor have been actively conducted (Cavallini et al., Alim Nutr. 2010. 21:175-182). For example, Ali and his colleagues examined effects on conversion into aglycone as an active form of metabolism of isoflavone glycoside by lactic acid bacteria and fat and cholesterol metabolism. According to the result, the lactic acid bacteria did not induce enhancement of efficacy of the isoflavone. The reason is that bioconversion efficiency by lactic acid bacteria is low (Ali, et al., J Nutr Biochem. 2004. 15:583-90). According to another report, conversion into aglycone by lactic acid bacteria bifidobacterium was 73 to 74% or less when soy milk was not added. However, in the case of adding the soy milk, the conversion rate increased to 84 to 85% (2007 11. Newhope 360.com).

Meanwhile, saponin is a glycoside of steroid, steroid alkaroid, or triterpene, and a general term of substances that dissolve in water and exhibit a foaming action like soap. The saponin is an ingredient for enhancing human immunity and specially, saponin included in ginseng is famous. In the ginseng, 32 types of various saponins are much included. Particularly, it is known that saponin included only in red ginseng obtained by processing the ginseng has a considerable effect in the treatment of adult diseases when administered for a long time. Ginsenoside may inhibit the growth of all kind of cancer cells. Even in the experiment related to cataract, the ginsenoside exhibited an excellent effect. Ginsenoside (ginseng saponin) is a compound that has carbohydrates (glycones) and non-carbohydrate residues (aglycones) in the same molecule. The carbohydrate residue binds to the non-carbohydrate residue through an acetal linkage at the 1-carbon position. The non-sugar component is referred to as an aglycone and the sugar component is referred to as a glycone. When the carbohydrate site is glucose, it is referred to as a glucoside. Accordingly, by the hydrolysis of ginsenoside which is the glycoside in ginseng, the ginsenoside is decomposed into the glycone and sapogenin as the aglycone.

Microorganisms that hydrolyze the isoflavone glycoside include *bifidobacterium longum, lactobacillus bulgaricus, aspergilus niger,* and *sachcaroplyspora erythraea*, and these microorganisms produce commonly β-glycosidase. In addition, researches for developing microorganisms that produce high-potency β-glycosidase capable of efficiently converting glycoside isoflavones into aglycone isoflavones have been continued.

However, the techniques in the related art include many complicated steps and thus there are problems such as a decrease in production rate, an increase in production cost, and possibility of contamination during a purifying process.

Under these technical backgrounds, the inventors of the present application have confirmed that conventional problems may be improved by converting glycosides into aglycones or hydrolyzed glycoside by using a microorganism producing β-glycosidase and then accumulating the converted aglycones or hydrolyzed glycoside in the microorganism and using a microorganism or a lysate containing the aglycones or hydrolyzed glycoside thereof as a raw material, and completed the present disclosure.

SUMMARY

An object to be achieved by the present disclosure is to provide a method of preparing a microorganism capable of preparing an aglycone or hydrolyzed glycoside converted from a glycoside in a high concentration by using a microorganism producing β-glycosidase.

Another object to be achieved by the present disclosure is to provide a microorganism or a lysate containing an aglycone or hydrolyzed glycoside thereof and a use thereof, in which the aglycone or hydrolyzed glycoside prepared by the method is accumulated in cells.

According to an aspect of the present disclosure, there is provided a method of preparing a microorganism in which an aglycone or hydrolyzed glycoside is accumulated in cells. The method comprises accumulating an aglycone or hydrolyzed glycoside converted from a glycoside in the microorganism by incubating the microorganism expressing β-glycosidase in a medium contaning glycoside or reacting with a reactant containing glycoside.

According to another aspect of the present disclosure, there is provided a microorganism or a lysate thereof which is prepared by the method and in which an aglycone or hydrolyzed glycoside is accumulated in cells.

According to yet another aspect of the present disclosure, there is provided a composition comprising the microorganism or the lysate thereof.

According to still another aspect of the present disclosure, there is provided a food comprising the microorganism or the lysate thereof.

According to still yet another aspect of the present disclosure, there is provided a composition for improving a skin function comprising the microorganism or the lysate thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 1, a raw material represents a culture medium containing soybean extracts, STD represents an isoflavone standard; and a *L. plantarum* K8-LTA extract represents a lysate lysed by using a microfluidizer after *Lactobacillus plantarum* K8 is incubated in a culture medium containing a soybean extract.

In FIG. 2, STD represents an isoflavone standard; delbrueckii represents *Lactobacillus delbrueckii*; GG represents *Lactobacillus rhamnosus* GG; K8 represents *Lactobacillus plantarum* K8; and sakei represents *Lactobacillus sakei*.

In FIG. 3, gg represents *Lactobacillus rhamnosus* GG, del represents *Lactobacillus delbrueckii*, and k8 represents *Lactobacillus plantarum* K8.

In FIG. 4, rg1, rg3(s), rh2, rb1 , rc, rd, rb2, and f2 are ginsenoside compounds. The above names are classified according to a molecular structure as kinds of saponin. In FIG. 4, washing represents a wash solution after incubating *Lactobacillus*; Ginseng ext represents a ginseng extract; and k8 represents *Lactobacillus plantarum* K8.

FIG. 9 is a table showing sugar availability of *Lactobacillus plantarum* k8.

In the related art, there have been attempts to convert a glycoside into an aglycone or hydrolyzed glycoside using a microorganism, but it is not yet reported that the converted aglycone or hydrolyzed glycoside is included in the cell of the microorganism. Accordingly, results of bioconversion into the aglycone or hydrolyzed glycoside by the microorganism according to the present disclosure and accumulation in the cells of the microorganism are new. The inventors of the present application confirmed that a concentration of the aglycone or hydrolyzed glycoside accumulated in the cells of the microorganism was more than 1.5 times, more than two times higher than that of the aglycone or hydrolyzed glycoside in a microbial culture medium to produce the aglycone or hydrolyzed glycoside in a high concentration.

As an action mechanism of probiotics, remodeling of an intestinal environment, inhibition of pathogens, inhibition of proinflammatory factors, an effect on epithelial differentiation, strengthening of an intestinal barrier effect, and the like are known. The actions of the probiotics on suppression of colorectal cancer have various biochemical pathways, and inhibit occurrence of colorectal cancer through a cell cycle, reactive oxygen species, apoptosis, production of specific bacterial enzymes, and a host metabolism. Further, lactic acid bacteria protect a body from diseases through an immune activation action that activates an immune system. In the villi of the intestinal surface, the lactic acid bacteria interact with immune cells such as leukocytes or lymphocytes and promotes the activity of immunity. The lactic acid bacteria induce the expression of human beta defensin (hBD2) in human colon cancer cells to regulate the intestinal immunity. Further, production of IL-8 which is inflammatory cytokine and inhibition of expression of Hsp70 are performed by exposure of lactic acid bacteria in Caco-2 cells which is colon cancer cells. As a result, it can be seen that the lactic acid bacteria is directly involved in the regulation of an inflammatory response by regulating cytokines. Further, the lactic acid bacteria in the intestine regulate an autoimmune response and a toll-like receptor (TLR). This means that the effect of the lactic acid bacteria on regulation of intestinal health is associated with TLR signaling.

Figure 5:
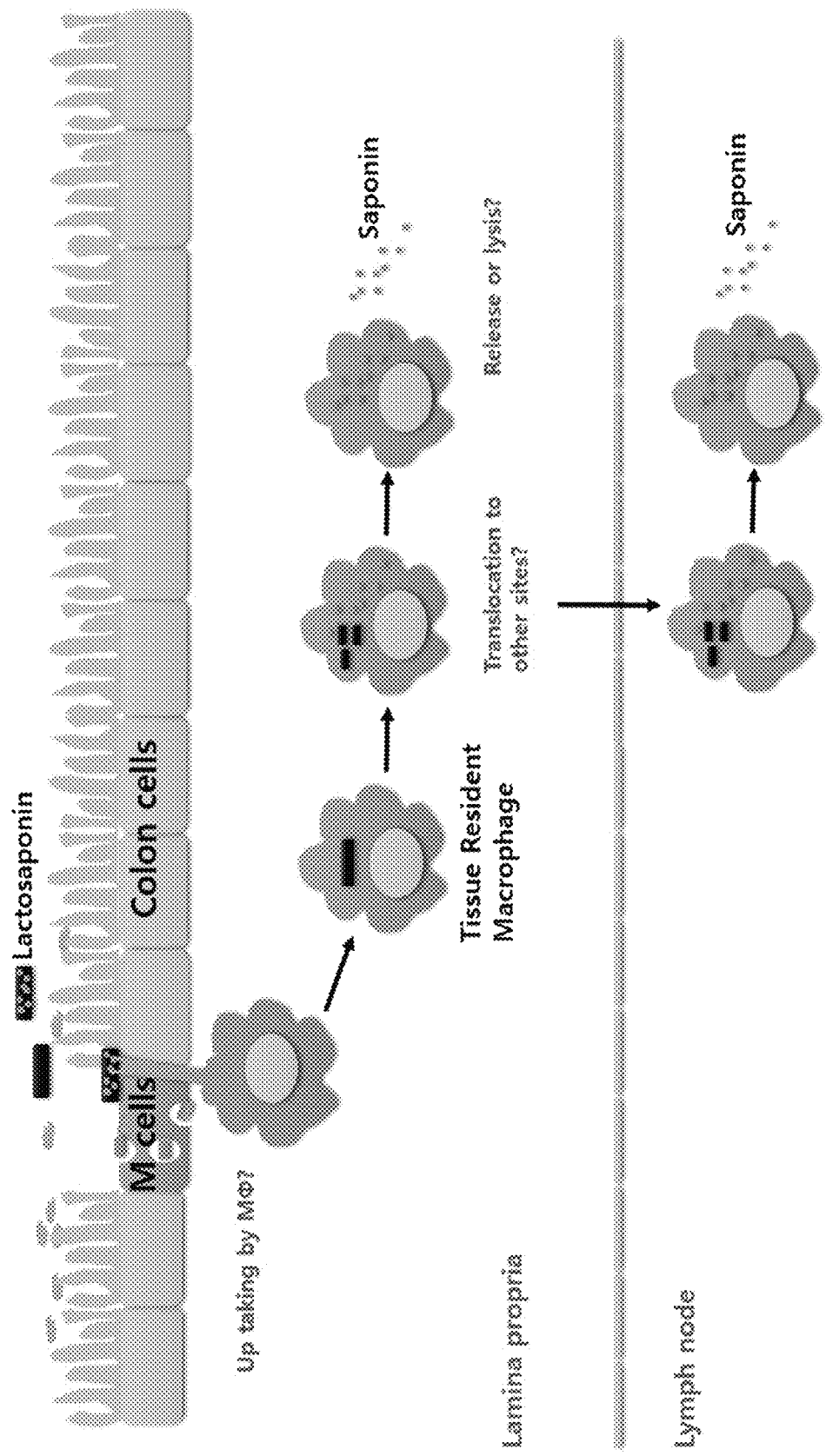
FIG. 5 is a diagram illustrating an absorption prediction mechanism of hydrolyzed saponin by *Lactobacillus plantarum* K8.

*Lactobacillus plantarum* K8 absorbs ginsenoside in a glycoside form and then decomposes the glycoside form into hydrolyzed saponin by using β-glycosidase. The sugars are used in the metabolism of the lactic acid bacteria, whereas since the hydrolyzed saponin are unnecessary substances for the metabolism of the lactic acid bacteria, the hydrolyzed saponin are accumulated in the body and then released outside the cells over time. The *lactobacillus plantarum* K8 containing the hydrolyzed saponin exhibited a body absorption rate 1,300 times or more higher than a case of taking ginsenoside (a saponin extract) which is not modified in a test using an animal (Example 7). The high absorption rate is because the *Lactobacillus plantarum* K8 serves as a capsule to prevent breakage of saponin and safely transfer the saponin to the intestines. Further, it is expected that the *Lactobacillus plantarum* K8 containing the hydrolyzed saponin is selectively up-taken by a tissue resident macrophage in the intestines and then moves to lamina propria or lymph node to release the hydrolyzed saponin to the blood (see FIG. 5).

Based thereon, an aspect of the present disclosure relates to a method of preparing a microorganism in which an aglycone or hydrolyzed glycoside is accumulated in cells. The method comprises accumulating an aglycone or hydrolyzed glycoside converted from a glycoside in the microorganism by incubating the microorganism expressing β-glycosidase in a glycoside-contained medium or reacting with a glycoside-contained reactant.

Figure 1:
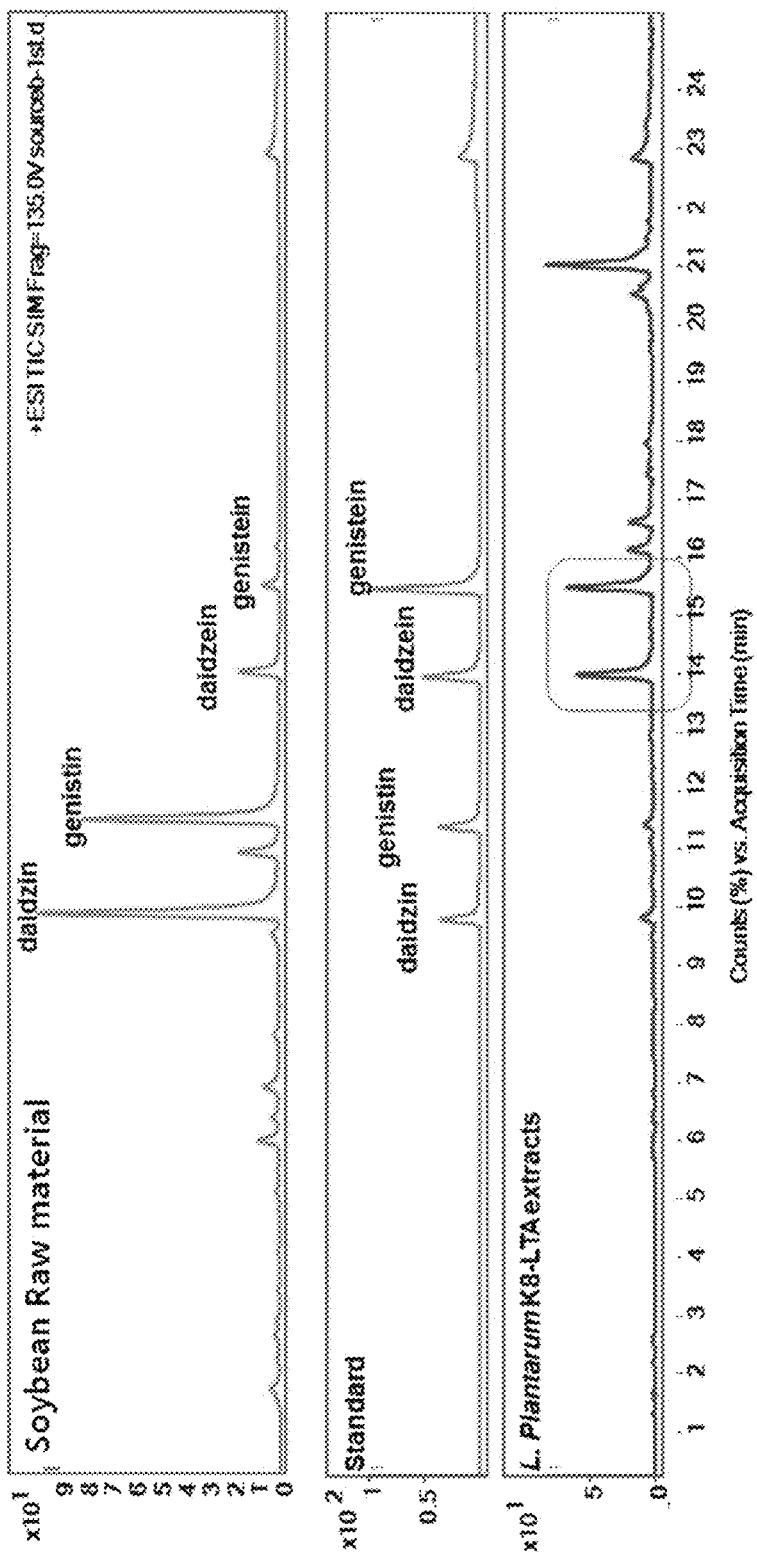
FIG. 1 illustrates a result of conversion into soybean aglycone using *Lactobacillus plantarum* K8 by a preparing method according to the present disclosure. Conversion of a glycoside isoflavone into an aglycone isoflavone by *Lactobacillus plantarum* K8.

The microorganism used in the present disclosure represents production activity of the aglycone or hydrolyzed glycoside. Particularly, the microorganism has ability of converting a glycoside into an aglycone form or hydrolyzed glycoside through the activity of β-glycosidase. Under an anaerobic condition, the microorganism has ability of converting glycoside forms genistin and diadzin to aglycone forms genistein and diadzein. In the case of lysing the microorganism, the aglycones accumulated in the cells may be detected (see FIG. 1).

The microorganism is not particularly limited as long as the microorganism is microorganisms producing β-glycosidase, but may be one or more selected from the group consisting of lactic acid bacteria, *lactococcus, corynebacterium*, generally recognized as safe (GRAS) microorganisms, bifidus, yeast, *bacillus, aspergillus* and *clostridium*. The lactic acid bacteria may be one or more selected from the group consisting of *L. plantarum, L. sakei, L. rhamnosus GG, L. delbrueckii, L. acidophilus, L. johnsonii, L. casei, L. gasseri*, and *Leuconostoc mesenteroid*.

The inventors of the present application isolated and identified *L. plantarum* K8 that produces β-glycosidase from Kimchi which is the Korean traditional fermented food. First, the kimchi and the kimchi liquid were diluted by 10 times in stages by using sterile physiological saline and then the undiluted solution and the diluted solution were spreaded on a *lactobacillus* selective agar (LBS agar, Difco). Colonies exhibited after incubating for 2 to 3 days at 37° C. were isolated again purely according to a type and a color. Gram staining and microscopic observation of the isolated colonies were performed and then only gram-positive and rod-shaped colonies were screened, and while these colonies were incubated in a *lactobacilli* MRS liquid medium (Difco) at pH 6.8 and 37° C. for 24 hrs, the colonies in which pH of the culture solution is decreased to 4.5 or less were re-screened. Thereafter, when the colonies were incubated for 2 hrs in a MRS medium at pH 2.0 and then incubated for 9 hrs in the MRS medium added with 0.3% of oxgall, the viable acid-resistant and biliary-resistant *lactobacillus* strains were isolated. The isolated strains were identified through a biochemical test using an API CHL 50 kit and 16S rRNA sequencing. As the identified result, it was confirmed that the strains were strains belonging to *Lactobacillus plantarum* species and the strains were called "*Lactobacillus plantarum* K8" (accession number: KCTC 10887BP).

In yet another example, the microorganism producing the β-glycosidase may be one or more selected from the group consisting of generally recognized as safe (GRAS) microorganisms, *Bifidus, Yeast, Bacillus licheniformis, S. thermophilus, L. casei, Streptomyces* sp. *Bifidobacteria, Lactobacillus delbrueckii* Rh2, *Sporosarcina* sp., *Saccharomyces cerevisiae, Pyrococcus furiosus, Lactobacillus plantarum, Aspergillus ochraceus, Lactobacillus delbrueckii* Rh2, *Pseudomonas* sp., *Aspergillus niger, Pseudomonas fluorescens, Bifidobacterium adolescentis, Aspergillus sojae, Cunninghamella blakesleeana, Bifidobacteria* and *Lactobacillus*, Lactic acid bacteria, *Bifidobacterium pseudocatenulatum, Penicillium melinii, Eubacterium ramulus, Clostridium orbiscindens, Aspergillus awamori, Lactobacillus brevis, Aspergillus parasiticus speare* BGB, *aspergillus aculeatus*, and *aspergillus niger.*

In order to prepare lactic acid bacteria comprising aglycone isoflavone or hydrolyzed saponin, *Lactobacillus plantarum* K8 was incubated in a medium added with a soybean extract or glycoside saponin and lysed by using a microfluidizer, and then the lysed *Lactobacillus plantarum* K8 was fractioned through a solvent system fraction. With respect to an EtOAc fraction with isoflavone or hydrolyzed saponin, the *Lactobacillus plantarum* K8 was prepared in a concentration of 2,000 ppm and then an analysis was performed by using LC-MS/MS. It can be confirmed that after lysing, the contents of daidzein and genistein as aglycone isoflavones and the content of Rg3 as an hydrolyzed saponin are increased.

The *Lactobacillus plantarum* K8 was lysed by using a sonicator or a microfluidizer and lyophilized to prepare a '*Lactobacillus plantarum* K8-LTA' lysate. Specifically, the step (a) may comprise the steps of static culture for microbial activation, shaking culture, and feeding culture in sequence. In this case, the microorganism may be static-cultured for 12 hrs at 37° C. and cultured with shaking under a condition of 6 rpm for 12 hrs at 37° C. A medium (for example, an MRS medium) composed of carbon sources, nitrogen sources, vitamins and minerals may be used for incubating the microorganism.

In some cases, before the step (a), a step of pre-treating the plant comprising the glycoside with a protease may be further included. The protease may be one or more selected from the group consisting of for example, promod, alkalase, neutrase, and papain.

Figure 8:
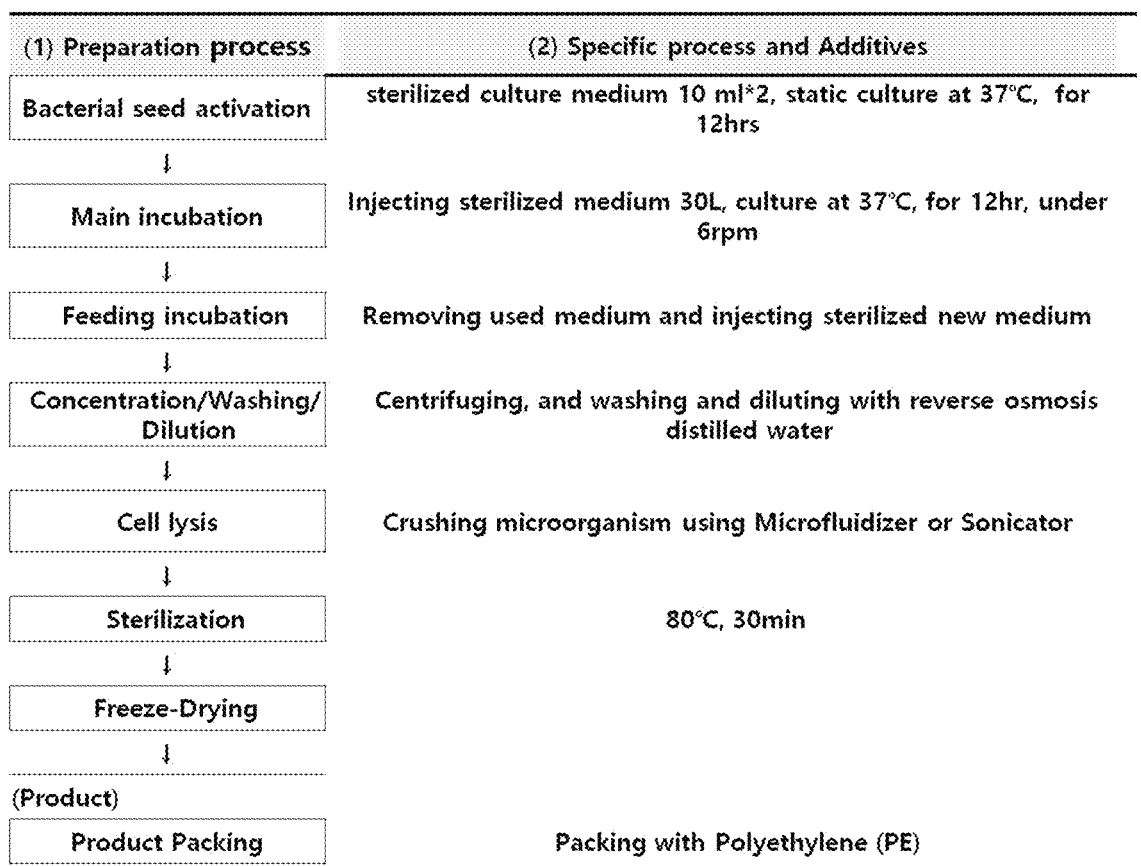
FIG. 8 is a table showing a preparation process according to the present disclosure.

In detail, detailed preparing processes are described in the following 'Preparing Process Table' and FIG. 8.

[Preparing Process Table] Membrane Cell-recycling Reactor (MCR) Preparing Process 1) Sterilization of fermentation line: A line flowing into a fermentation pipe is sterilized by using the steam.

2) Co-sterilization of fermentation tank and feeding tank: The fermentation tank and the feeding tank are sterilized for 15 to 20 minutes under a condition of 121±1° C. and 1.2 to 1.5 kgf/cm$^2$ by injecting the steam into the tank by using a sparger, sampling, and a lower steam.

3) Weighting of raw materials and sterilization of medium: Raw materials of a culture medium are accurately weighted according to the standard of the product, respectively, and then injected into both the fermentation tank and the feeding tank and sterilized according to a condition 2) after adjusting the amounts according to a capacity.

4) Cooling: Cooling is performed to 37° C. after sterilization.

5) Bacterial seed activation: The frozen *lactobacillus* are rapidly thawed in a 37° C. thermostatic bath and then inoculated in a sterilized culture medium of 1.5 L and static-cultured for 12 hours.

6) Main incubation: The bacterial seed diluted with 1/100 is incubated in a sterilized main culture medium of 30 L.

7) Feeding incubation: The incubation conditions are frequently checked so as to be maintained at all times. When an optical density (OD) value reaches a predetermined value, a used medium is removed by circulating the membrane and a new medium is injected to the feeding tank by a discharged amount. The bacterial cells are incubated by continuously removing and injecting a medium of about 200 L.

8) Concentration adjustment: A drain line is sterilized with steam for 30 minutes, and then a solution flows through the drain line and centrifuged, and diluted with an appropriate amount of reverse osmosis distilled water to adjust the concentration.

9) collection of live cells and product packaging or lysing of bacterial cells: The concentration-adjusted bacterial cells are lysed by a microfluidizer.

10) steriliztion: The lysed bacterial cells are maintained for 30 minutes at 80° C. and the medium solution is sterilized and cooled again. According to a purpose, the steriliztion may be excluded.

11) Collection and packaging of bacterial cells: The cooled solution is contained and packaged in a polyethylene (PE) bottle by using a tank drain line.

In yet another example, the microorganism is inoculated and then incubated in a medium, and transferred to a minimal medium comprising a glycoside, and may be additionally cultured for 1 to 36 hrs, for example, 4 to 24 hrs. According to Example 6 of the present disclosure, when the microorganism is incubated by using the minimal medium comprising the glycoside, it is confirmed that the accumulation of the aglycone or hydrolyzed glycoside in the cells may be increased compared with a control group in which the same amount of cells is incubated in the MRS medium comprising the glycoside saponin.

In one example, the glycoside may be originated from one selected from the group consisting of ginseng, wild ginseng, soybean, codonopsis lanceolata, buckwheat, bellflower, water parsley, mung beans, garlic, onion, ginkgo, and kudzu.

The glycoside may be an isoflavone glycoside, a saponin glycoside, a phenol glycoside (phenol), a cynophore glycoside (a nitrile glycoside), an anthraquinone glycoside, a cardiac glycoside, a bitter glycoside (amara), a coumarin glycoside (coumarin), a sulfur glycoside (a rioglycoside and a sulfur), or an flavonoid glycoside (flavonoid). For example, the method according to the present disclosure may be converting one or more glycosides selected from the group consisting of daidzin, genistin, glycitin, saponin, procyanidin, naringenin, quercetin, rutinose, hesparidin, baicalin, wogonoside, mogroside V, amygdalin, and 3-phenyl coumarin into one or more hydrolyzed glycoside selected from the group consisting of genistein, daidzein, glycitein, hydrolyzed saponin , 3,4-Hydroxyphenylactic acid, 4-HPA, m-coumaric acid, p-coumaric acid, O-beta-D-glucuroniodes, stilbenoids, rutin, quercetin, hesparetin, baicalein, wogonin, mogroside IIIE, mendelonitrile, benzaldehyde, and coumarin-derived compounds.

The aglycones or hydrolyzed glycoside produced by the preparing method may be accumulated in the cells. Based thereon, another aspect of the present disclosure relates to a microorganism or a lysate thereof in which an aglycone or hydrolyzed glycoside produced by the preparing method is accumulated in cells. It is confirmed that the concentration of the aglycone or hydrolyzed glycoside accumulated in the cells is two times higher than that of the aglycone or hydrolyzed glycoside in a microbial culture medium.

The lysate may be prepared by using a physical method. For example, the microorganism may be lysed 4 to 9 times by using bead mills, presses, a sonicator, or a microfluidizer and then lyophilized and powdered. If necessary, the lysed bacterial cells are maintained for 30 minutes at 80° C. and the medium solution may be sterilized and cooled again.

Yet another aspect of the present disclosure relates to a composition comprising the microorganism or the lysate thereof.

The microorganism or the lysate thereof may be used as an antioxidant composition, a composition for intestinal regulation, a raw material composition for cosmetics, and a probiotic composition. Particularly, the microorganism or the lysate thereof may be used as a feed composition, a composition for food addition, and other fermented products. The lysed cell wall fractions of the microorganism or the lysate thereof according to the present disclosure, lived microbes, dead microbes, dried microbes or cultures may be included as an active ingredient, and excipients or carriers may be additionally included.

The culture comprises a culture solution itself incubated in a liquid medium, a filtrate (a centrifuged supernatant) obtained by filtering or centrifuging the culture solution to remove the strain, and a cell lysate obtained by ultrasonicating or lysozyming the culture solution. The content of the microorganism or the lysate thereof in the composition of the present disclosure may vary according to a use and a formulation of the composition.

The composition according to the present disclosure may be prepared and administered by various formulations and methods. For example, the microorganism or the lysate thereof or the culture is combined with a carrier or a flavoring which is generally used in a pharmaceutical field and then may be prepared and administered in forms such as tablets, troches, capsules, elixirs, syrups, powders, suspensions, or granules. As the carriers, binders, lubricants, disintegrants, excipients, solubilizers, dispersants, stabilizers, suspending agents, and the like may be used. The administering method may use an oral, parenteral, or applying method, and a dose may be appropriately selected according to the absorption, the inactivity rate, and the excretion rate of active ingredients in the body, and age, gender, status, and the like of persons to be administered. Preferably, the composition may be administered with an effective dose of 10 mg/day, and in the case of a probiotic composition, the viable cell count in the composition may be $10^8$ to $10^{10}$ CFU/day.

The antioxidant composition may be used for removing active oxygen, and the intestinal regulation composition or the probiotic composition promotes the internal absorption of isoflavone to prevent or improve dyspepsia or diarrhea.

Further, the feed composition may be prepared in forms such as fermented feed, compound feed, a pellet form, silage, and the like. The fermented feed may be prepared by fermenting organic materials by adding the microorganism or the lysate thereof of the present disclosure and various other known microorganisms or enzymes, and the compound feed may be prepared by combining various kinds of regular feeds and the lactic acid bacteria of the present disclosure. The pellet form feed may be prepared by formulating the fermented feed or the compound feed by a pellet machine and the silage may be prepared by fermenting green feed with the lactic acid bacteria according to the present disclosure.

Further, the microorganism or the lysate thereof or the culture thereof may be used as food additives for foods such as baby foods, kimchi, beverages, dairy products, and the like.

Further, the present disclosure relates to food comprising the microorganism or the lysate thereof.

The microorganism or the lysate thereof of the present disclosure or the culture thereof may be used as a cosmetic composition, and specifically, may used for various uses such as basic cosmetics, cosmetics, hair cosmetics, whitening cosmetics, wrinkle cosmetics, and anti-aging cosmetics.

Furthermore, the present disclosure provides a composition for improving a skin function comprising the microorganism or the lysate thereof. The improvement of the skin function may mean improve skin moisturizing, skin color, skin elasticity, wrinkles or dermis density.

Further, the microorganism or the lysate thereof according to the present disclosure may be used as a starter for preparing fermented products. The fermented products include fermented meat products such as ham and sausage, fermented raw food products, fermented milk products, fermented soybean liquids, kimchi, and the like. The fermented products may be prepared according to general methods known in the art. For example, the fermented raw food products may be prepared by combining the microorganism or the lysate thereof with grain powder such as brown rice and adlay, vegetable powder, and mushroom powder or prepared by fermenting the grain powder with the microorganism or the lysate thereof or two to five types of mixed lactic acid bacteria comprising the microorganism or the lysate thereof at an appropriate temperature and then appropriately combining the vegetable and mushroom powder to have excellent nutritional balance and palatability. Further, the fermented milk products may be prepared by fermenting raw milk or skimmed milk powder with the lactic acid bacteria according to the present disclosure or two to five types of mixed lactic acid bacteria comprising the same at an appropriate temperature, and the fermented soybean liquid may be prepared by fermenting a soybean liquid with the lactic acid bacteria according to the present disclosure or two to five types of mixed lactic acid bacteria comprising the same at an appropriate temperature.

Hereinafter, the present disclosure will be described in detail by Examples. However, the following Examples just exemplify the present disclosure, and the contents of the present disclosure are not limited to the following Examples.

EXAMPLES

Example 1: Biochemical Characteristic Test of *Lactobacillus Plantarum* K8

In order to evaluate the antioxidant activity of *Lactobacillus plantarum* K8 isolated and identified from kimchi which was the Korean traditional fermented food, an API test (Biomerieux, France) was performed. Biochemical characteristics and sugar availability of the lactic acid bacteria were as listed in Table 1 below and in FIG. 9.

TABLE 1

| characteristics of *Lactobacillus plantarum* k8 | |
| --- | --- |
| Characters | Results |
| Type of bacteria | Bar Type |
| Optimum growth temperature | 37° C. |
| Motility | No |
| Gram-Staining | + |
| Activity to Catalase | − |
| Influence of oxygen | Oblivious anaerobic |

Example 2: Production of Aglycone of *Lactobacillus Plantarum* K8

*Lactobacillus plantarum* k8 was incubated in a medium added with soybean extracts and lysed by using a microfluidizer, and then the lysed *Lactobacillus plantarum* K8 was fractioned by a solvent fraction system. With respect to an EtOAc fraction with isoflavone, the *Lactobacillus plantarum* K8 lysate sample was prepared in a concentration of 2000 ppm and then an analysis was performed by using LC-MS/MS. As a result, it was confirmed that in the case of soybean raw materials, the contents of daidzin and genistin as glycoside isoflavones were high, whereas after incubation with *Lactobacillus plantarum* K8, the contents of daidzein and genistein as aglycone isoflavones were increased. On the contrary, the contents of the glycoside isoflavones were reduced in the media after incubation with *Lactobacillus plantarum* K8 (see FIG. 1). Before the *Lactobacillus plantarum* K8 according to the present disclosure was inoculated, in the case of including a pre-treatment process of stirring for 8 hrs at 60° C. by adding 1 ml/L of alkalase, 1 ml/L of neutrase and 0.2 g/L of papain, the intracellular accumulation rate after the conversion into the aglycone was increased by about 10% (Table 2).

TABLE 2

| Intracellular accumulation rate after the conversion into the aglycone by enzyme pre-treatment | | |
| --- | --- | --- |
| | daidzein (ng/mL) | genistein (ng/mL) |
| No treatment of enzyme* | 8,672.46 | 18,286.58 |
| pre-treatment of enzyme | 9,539.24 | 20,115.24 |

Example 3: Evaluation of Production Activity of Aglycone

Figure 2:
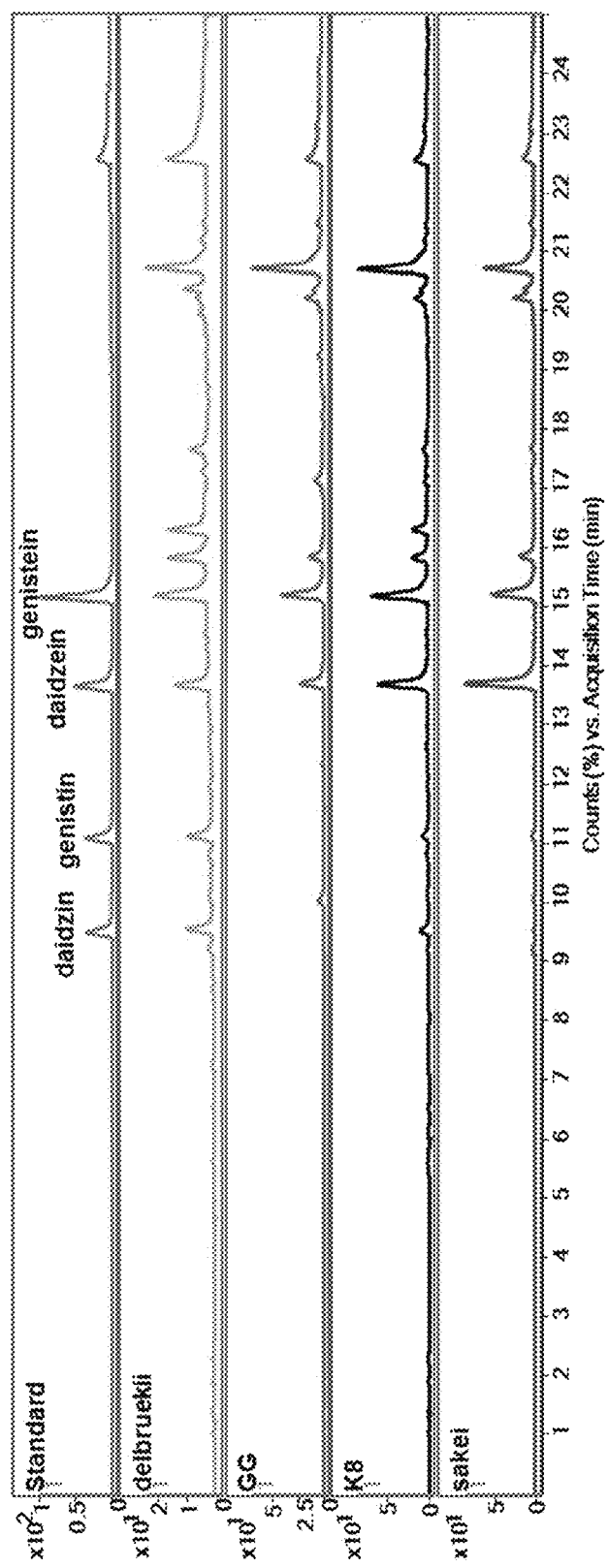
FIG. 2 illustrates a result of conversion into a soybean aglycone by using *Lactobacillus plantarum* K8, *Lactobacillus delbrueckii, Lactobacillus rhamnosus* GG, and *Lactobacillus sakei* by the preparing method according to the present disclosure. Comparison of production of aglycones of *Lactobacillus* including *Lactobacillus plantarum* K8.

In order to determine conversion ability of the aglycone isoflavone of the lactic acid bacteria and accumulation ability of the aglycone isoflavone in the cells, L. delbrueckii, L. rhamnosus GG, L. plantarum K8, and L. sakei were inoculated in a culture medium including soybean extracts and incubated for 12 hrs at 37° C., and then the cells were lysed by using a microfluidizer. In the lysed cells, the content of isoflavone was measured by LC/MS-MS and illustrated in FIG. 2. As a result, the aglycones of daidzein and genistein were detected in 4 types of *lactobacillus* (see FIG. 2). The result means that the glycoside isoflavone may be bioconverted into the aglycone isoflavone by all kinds of *lactobacillus* or microorganisms secreting β-glycosidase, and further, the result exhibits that the converted aglycone isoflavone may be accumulated in the cells.

Figure 3:
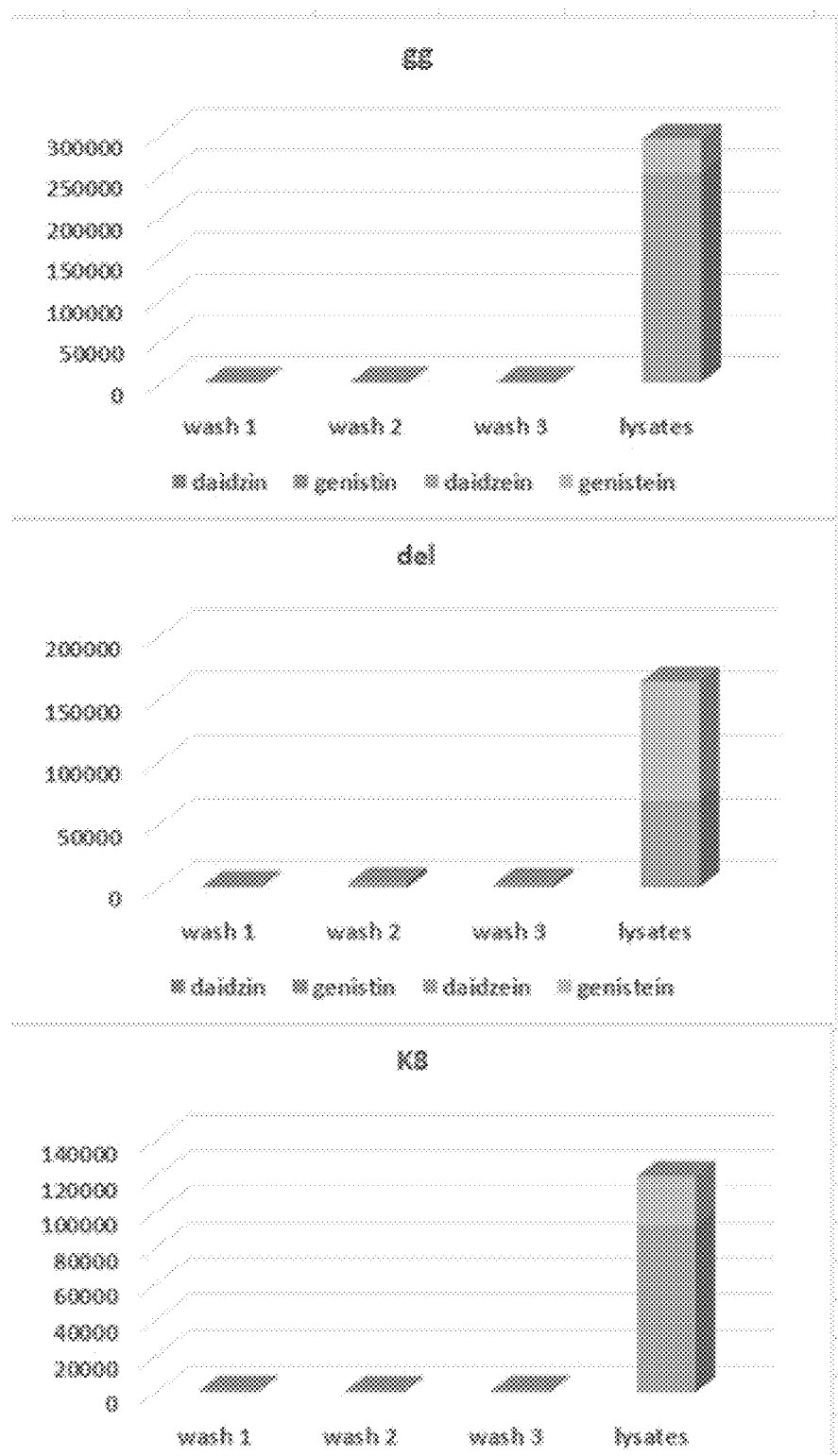
FIG. 3 illustrates a measured quantity of a soybean aglycone detected in a preparing process of *Lactobacillus plantarum* K8 lysates by the preparing method according to the present disclosure.

Example 4: Production Activity of Aglycone Isoflavone for Each Process of Lactic Acid Bacteria Experiments for measuring the isoflavone content during the production of the lactic acid bacteria lysate were performed. L. rhamnosus GG, L. delbrueckii, and L. plantarum K8 were incubated in a culture medium including soybean extracts for 12 hrs at 37° C. and then washed three times by using sterilized water. The isoflavone contents of the wash liquid and the *lactobacillus* lysates were measured by using the LC/MS-MS, respectively. As a result, the glycoside isoflavones were not detected from the three-time wash liquid and the lactobacillus lysates. Meanwhile, in the case of the aglycone isoflavones, a small amount was detected from the wash liquid and the aglycone isoflavone was detected from the *lactobacillus* lysates in a high concentration (see FIG. 3). In another experiment, the contents of glycoside and aglycone isoflavones were measured in *Lactobacillus plantarum* K8 culture media, culture supernatant (sup.), wash 1-time, 2-time and 3-time, lysates, lysates supernatant (sup.), and lysates precipitate (ppt.). As a result, it was confirmed that in the lysates, the lysates sup., and the lysates ppt., the content of isoflavone, particularly, aglycone isoflavone was largely increased (see Table 3). In the result, the aglycone isoflavone may not be smeared on the surface of lactic acid bacteria or caused by the residual culture solution, and thus, the result means that the aglycone isoflavone is accumulated in the lactic acid bacteria.

TABLE 3

Comparison of aglycone isoflavone amount according to process of preparation

| No. | Name | daidzin (ng/mL) | genistin (ng/mL) | daidzein (ng/mL) | genistein (ng/mL) |
|---|---|---|---|---|---|
| 1 | Media | 3,689.6 | 2,385.1 | 4,394.1 | 1,857.2 |
| 2 | Culture sup. | 398.3 | 372.3 | 1,139.2 | 1,796.8 |
| 3 | Wash 1 | N.D.* | 2,431.7 | 3,163.1 | 1,588.3 |
| 4 | Wash 2 | N.D. | 673.2 | 6,552.7 | 8,727.3 |
| 5 | Wash 3 | N.D. | 1,800.0 | 6,638.2 | 4,601.0 |
| 6 | Lysates | N.D. | N.D. | 36,545.1 | 101,626.4 |
| 7 | Lysates sup. | 3,823 | 1,2276.5 | 12,272.1 | 8,785.7 |
| 8 | Lysates ppt. | N.D. | 291.1 | 37,907.4 | 72,453.7 |

*N.D.: not determined

Example 5: Conversion of Saponin by Lactic Acid Bacteria

Figure 4:
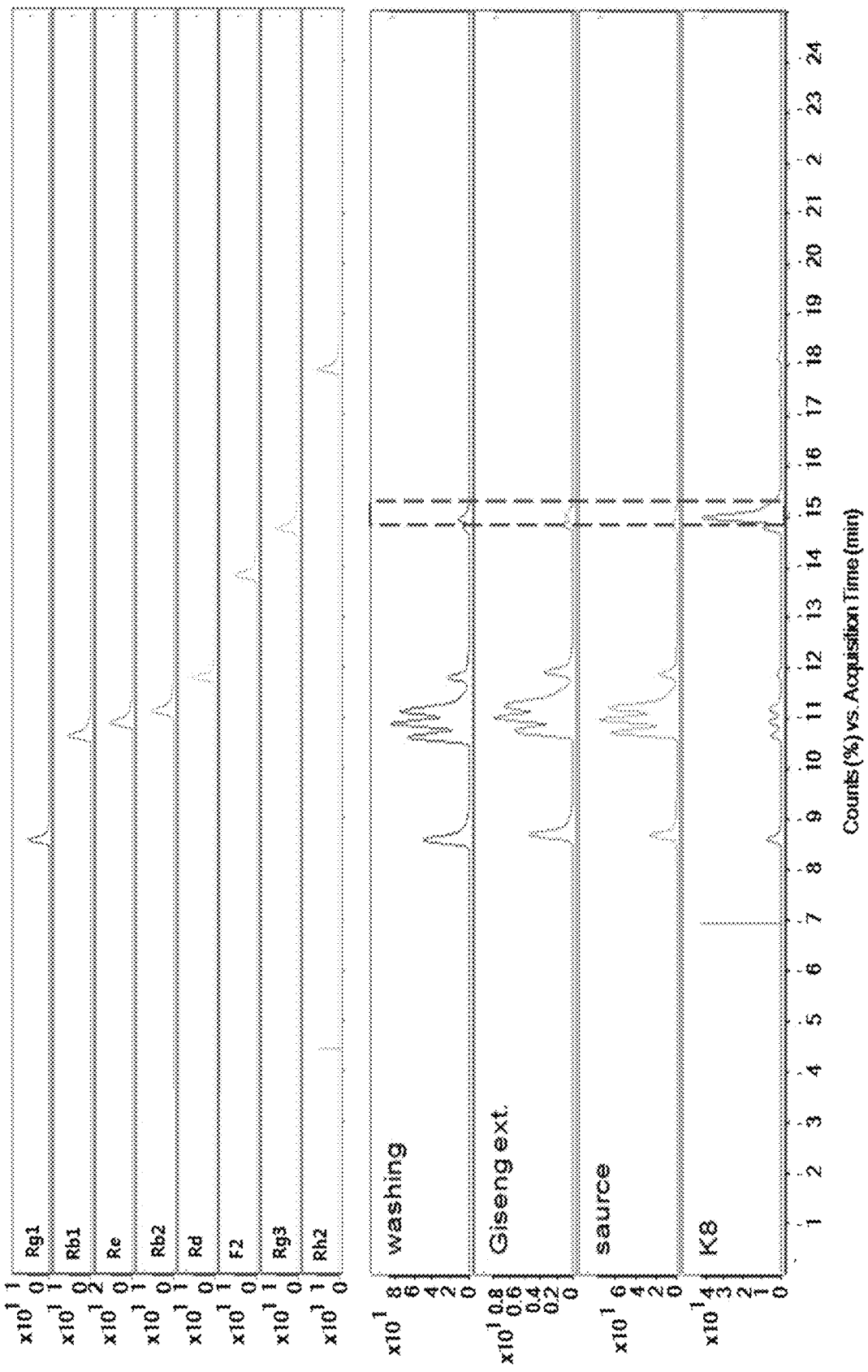
FIG. 4 is a graph illustrating saponin converted from ginsenoside by using *Lactobacillus plantarum* K8 by the preparing method according to the present disclosure.

In order to determine conversion of ginseng saponin into hydrolyzed saponin and intracellular accumulation, *Lactobacillus plantarum* K8 was incubated in a culture solution added with ginseng extracts and then the *Lactobacillus plantarum* K8 was lysed by using a microfluidizer. After lysing, ginsenoside compounds were analyzed by LC/MS-MS. As a result, it was confirmed that *Lactobacillus plantarum* K8 uptook in ginsenoside in the same context as the result of isoflavone (see FIG. 4, comparison of area values of washing and lysates). That is, peaks which were not exhibited in the wash liquid and the ginseng extracts were exhibited in the lactic acid bacteria lysates, and it can be seen that the peaks are transformed by enzymes of the lactic acid bacteria (see FIG. 4, represented by a dotted box). The key point of ginsenoside conversion is the conversion of ginsenoside which has a large amount and low activity into ginsenoside of Rg3, Rc, and F2 which have a small amount, but excellent activity. In the experimental result, it can be confirmed that the ginsenoside is converted into Rg3 which is a kind of high-grade saponin by *Lactobacillus plantarum* K8.

Example 6: Increase in Intracellular Accumulation of Hydrolyzed Saponin Using Minimal Medium

*Lactobacillus plantarum* K8 was inoculated in 5 mL of an MRS medium and then static-incubated for 24 hrs at 37° C. and transferred to 50 mL of the MRS medium and additionally incubated for 12 hrs. The incubated cells were transferred to 1 L of the MRS medium and incubated for 15 hrs, and then washed with PBS three times. The washed cells were inoculated in 1 L of a M9 minimal medium including saponin glycoside and a MRS medium including saponin glycoside and lysozyme (0.5 g/L) by the same number and then static-incubated for 6 hrs. In yet another experiment, the cells were transferred to a MRS medium including saponin glycoside and incubated for 6 hrs at 42° C. As a control group, the same amount of cells was incubated in the MRS medium including saponin glycoside for 6 hrs. The incubated cells were washed and then lysed by using a microfluidizer, and the ginsenoside compounds were analyzed by LC/MS-MS. In the case of cells using the M9 minimal medium, the aglycone sapogenin compound is 3.84 times or more greater than that of the control group (see Table 4).

TABLE 4

Comparison in detected amount of hydrolyzed saponin depending on culture conditions of *Lactobacillus plantarum* K8

| | total area | BuOH fr. (mg) | relative ratio |
|---|---|---|---|
| MRS (Lysozyme) | 7545 | 6.6 | 0.32 |
| MRS (Heat shock) | N.D. | 5.6 | — |
| minimal medium (M9) | 40762 | 12.4 mg | 3.84 |
| MRS | 17779 | 7.4 mg | 1 |

Example 7: Detection of Ginsenoside from Blood of Mice

Figure 6:
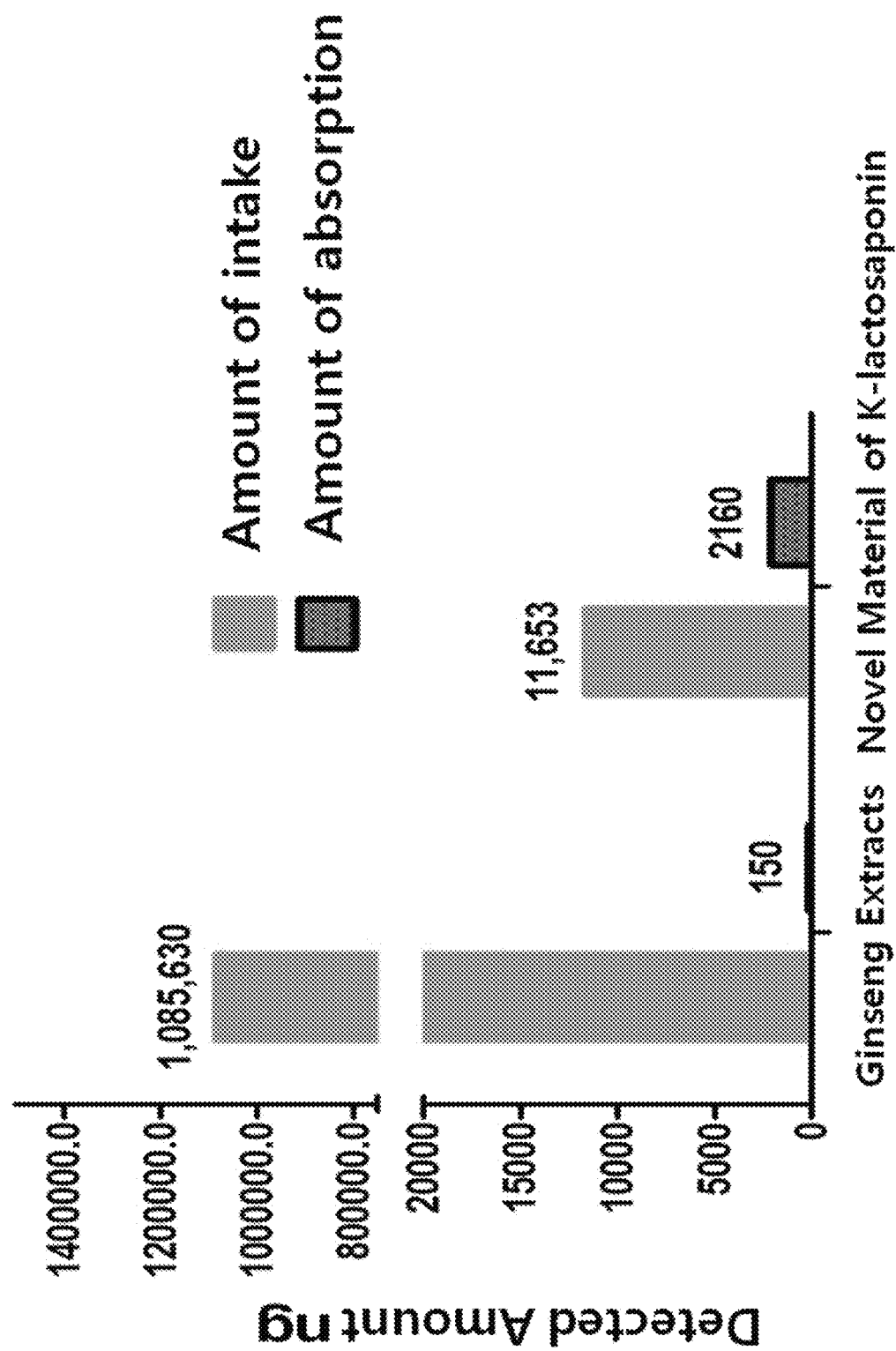
FIG. 6 illustrates a result of measuring detection amounts of low molecular ginsenoside. An intake amount represents an amount of a ginseng extract fed to mice and an absorption amount represents an amount of a ginsenoside detected from the blood of the mice.
Figure 7:
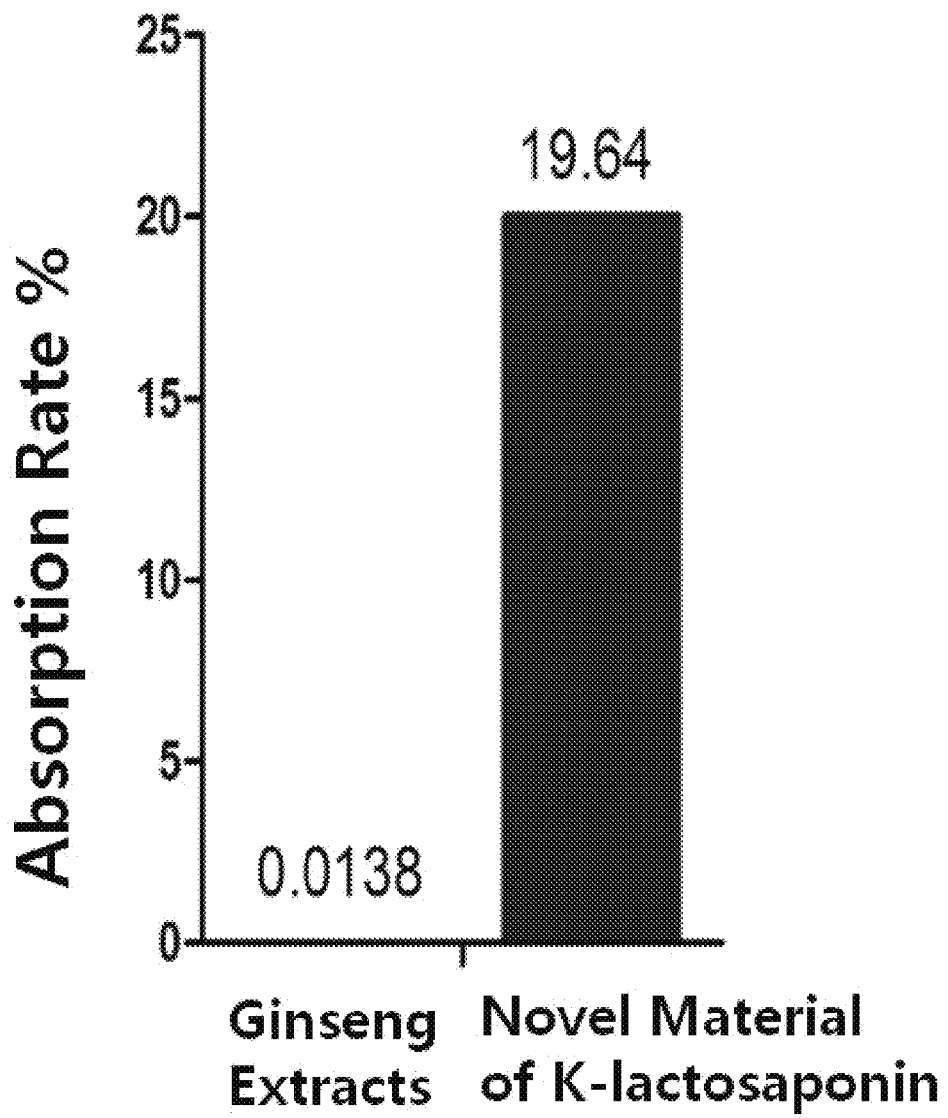
FIG. 7 is a result illustrating an absorption rate of a low molecular ginsenoside. The absorption rate is a result of converting an absorbed amount in the intake amount to a percentage.

The content of ginsenoside was measured in the blood isolated from mice uptaking ginseng extracts and functional hydrolyzed saponin -containing *Lactobacillus plantarum* K8 for 3 days. In the case of the ginseng extracts, the ginsenoside of about 150 ng of 1,085,630 ng of a total taking amount was absorbed. Meanwhile, the amount of the ginseng extracts taken in by the hydrolyzed saponin-containing *Lactobacillus plantarum* K8 was 11,653 ng and a total content of the ginsenoside detected from the blood was about 2160 ng (see FIG. 6). When converting the contents into a percentage, in the case of the ginseng extracts, an absorption rate of 0.014% was exhibited, but the absorption rate of the ginsenoside by the hydrolyzed saponin-containing *Lactobacillus plantarum* K8 reaches about 20% (see FIG. 7).

Particularly, in the mice taking the hydrolyzed saponin-containing *Lactobacillus plantarum* K8, a large amount of F2 and Rg3 ginsenoside are absorbed, and it is known that the F2 and Rg3 have the most excellent functionality even in the ginsenoside.

Although a large amount of ginseng extracts is taken, there is no large meaning in the taking amount due to low absorption rate. Meanwhile, in the case of the hydrolyzed saponin-containing *Lactobacillus plantarum* K8, the absorption rate is about 1300 times or more greater than that in the case where the ginseng extracts are directly taken. That is, when 100 g of the ginseng extracts is directly taken, 99% or more of the taking amount is not absorbed but discarded, but 20 g of the hydrolyzed saponin-containing *Lactobacillus plantarum* K8 may be absorbed. The result means that low-molecular ginsenoside in the hydrolyzed saponin-containing *Lactobacillus plantarum* K8 is naturally protected by the lactic acid bacteria during the digestive process of mice.

Example 8: Intracellular Accumulation of Hydrolyzed Saponin Using Yeast

Saccharomyces cerevisiae was inoculated in 5 ml of a YPD medium and shaking-incubated for 24 hrs at 37° C., and then transferred to 500 ml of a YPD medium added with ginseng extracts (1 g/L) and then additionally incubated for 12 hrs. After centrifuging, a supernatant was separately refrigerated and a pellet was washed 3 times with sterile distilled water. The washed yeast was lysed three times by using a microfluidizer and then aglycone ginsenoside compounds were analyzed through LC/MS-MS. In the present experiment, a total of six groups of samples prepared for analysis were divided into a supernatant after incubation (1), wash 1-time (2), wash 2-time (3), wash 3-time (4), before lysing (5), and after lysing (6). The result is listed in Table 5 below.

TABLE 5

Preparation of *Saccharomyces cerevisiae* comprising hydrolyzed saponin

| Sample | hydrolyzed saponin (ng/mL) |
|---|---|
| Culture medium (1) | 675 |
| Washing 1 (2) | 175 |
| Washing 2 (3) | 165 |
| Washing 3 (4) | 245 |
| Before lysis (5) | 45 |
| After lysis (6) | 1,222 |

Example 9: Clinical Trial Result on Candy Including *Lactobacillus Plantarum* K8 Lysate In order to evaluate efficacy of human skin moisturizing and skin color improvement for *Lactobacillus plantarum* K8 lysates (*Lactobacillus plantarum* K8-LTA), clinical trials were performed. The present research was performed based on the request contents of the client and guidelines for the human application test (established by the Korea Food and Drug Administration in December, 2011), human application tests of health functional foods (Korea Food & Drug Administration, in Deceber, 2008) and guideline for good clinical practice (GCP), and the approval of the Clinical Study Deliberation Committee of Kyung Hee University (Study No. KHUSBC 2012-011) was obtained.

41 female subjects aged 25 to 60 who had dry skin and whose skin color began to be dull or had already been dull were selected and on an empty stomach, the products (Table 25) were taken in with 2 tablets in the morning and 2 tablets in the evening. A test product (candy including 2.1% *Lactobacillus plantarum* K8-LTA) and a control product (candy without including 2.1% *Lactobacillus plantarum* K8-LTA) were allocated double-blind randomly to the selected subjects and administered for 8 weeks, and thereafter, at respective time points of before using the test product, in 4 weeks after using, and in 8 weeks after using, a skin improvement effect was evaluated by performing skin color visual evaluation, skin moisture, dead skin quantity, TEWL, skin color ($L^*$ value) and questionnaire evaluation, safety evaluation, dietary survey, and weight (including BMI) survey. Further, before the product administration and in 8 weeks after the product administration, the blood analysis was performed. It was confirmed that the candy including *Lactobacillus plantarum* K8-LTA included the aglycone isoflavone through an analysis of LC/MS-MS.

1. Visual Evaluation Result

As compared with before administering the product, skin color (brightness) was significantly improved (decreased) statistically in both the control group and the test group in 4 weeks and 8 weeks after the product administration. In comparison between the groups, in 4 weeks and 8 weeks after the product administration, there is no statistically significant difference between the groups ($p<0.05$).

2. Device Evaluation 2-1. Skin Moisture Amount

As compared with before the product administration, in 4 weeks after the product administration, the skin moisture at the face and the forearm was statistically significantly increased in both test groups, and in 8 weeks after the product administration, the skin moisture at the face was statistically significantly increased in both the test group and the control group, and the skin moisture at the forearm was statistically significantly increased in the test group. In comparison between the groups, in 4 weeks and 8 weeks after the product administration at the face and in 4 weeks after the product administration at the forearm, as compared with the control group, in the test group, the skin moisture was statistically significantly increased ($p<0.05$) (Table 6).

TABLE 6

Changes in moisture amount between groups

| Site | Weeks | Group | Δ Mean ± S.D. (A.U) | p-value† |
|---|---|---|---|---|
| Face | 4 | Control | 0.64 ± 0.48 | 0.000***^ |
|  |  | Test | 6.47 ± 1.14 |  |
|  | 8 | Control | 2.39 ± 0.61 | 0.007** |
|  |  | Test | 8.10 ± 1.86 |  |
| Forearm | 4 | Control | 0.49 ± 0.44 | 0.030* |
|  |  | Test | 2.22 ± 0.62 |  |
|  | 8 | Control | 1.35 ± 1.04 | 0.068^ |
|  |  | Test | 4.14 ± 0.84 |  |

†p-value: Independent t-test (*$p < 0.05$, $p < 0.01$, *$p < 0.001$)
†p-value^: Mann-Whitney test

2-2. Transepidermal Water Loss (TEWL)

As compared with before the product administration, in 8 weeks after the product administration, at the face and the forearm, TEWL was statistically significantly decreased in both test groups. In comparison between the groups, in 8 weeks after the product administration, at the forearm, the TEWL was statistically significantly decreased in the test group as compared with the control group ($p<0.05$) (Table 7).

TABLE 7

Comparison of Transepidermal water loss between groups

| Site | Group | Weeks | Δ Mean ± S.D. (g/m²h) | p-value† | IF°(%) |
|---|---|---|---|---|---|
| Face | Control | 0 | 13.02 ± 2.15 | — | — |
| | | 4 | 13.21 ± 2.12 | 0.392 | ▲1.46 |
| | | 8 | 12.76 ± 2.08 | 0.330 | ▼1.20 |
| | Test | 0 | 12.98 ± 1.83 | — | — |
| | | 4 | 12.90 ± 2.05 | 0.837 | ▼0.62 |
| | | 8 | 11.93 ± 1.62 | 0.008** | ▼8.09 |
| Forearm | Control | 0 | 6.89 ± 1.16 | — | — |
| | | 4 | 6.90 ± 1.16 | 0.936 | ▲0.15 |
| | | 8 | 6.61 ± 1.31 | 0.187 | ▼4.06 |
| | Test | 0 | 7.56 ± 1.04 | — | — |
| | | 4 | 7.35 ± 1.35 | 0.303 | ▼2.78 |
| | | 8 | 6.50 ± 1.33 | 0.002**^ | ▼14.02 |

†p-value: Paired t-test (*p < 0.05, p < 0.01, *p < 0.001)
†p-value^: Wilcoxon singled rank test.
°Intensification factor(IF): (W X − W 0)/W 0 × 100, calculated by mean value

2-3. Dead Skin Quantity

As compared with before the product administration, in 4 weeks and 8 weeks after the product administration, at the face, the dead skin quantity was statistically significantly decreased in the test group and at the forearm, the dead skin quantity was statistically significantly decreased in both the control group and the test group. In comparison between the groups, at both the face and the forearm, in 4 weeks and 8 weeks after the product administration, as compared with the control group, in the test group, the dead skin quantity was statistically significantly decreased ($p<0.05$) (Table 8).

TABLE 8

Changes in dead skin quantity between groups

| Site | Weeks | Group | Δ Mean ± S.D. (pixels) | p-value† |
|---|---|---|---|---|
| Face | 4 | Control | 272.35 ± 3,795.82 | 0.002** |
| | 4 | Test | −14,696.67 ± 2,306.89 | 0.002** |
| | 8 | Control | −7,373.50 ± 4,395.46 | 0.000*** |
| | 8 | Test | −38,263.71 ± 3,653.16 | 0.000*** |
| Forearm | 4 | Control | −29,518.20 ± 4,504.67 | 0.007**^ |
| | 4 | Test | −48,557.33 ± 5,394.31 | 0.007**^ |
| | 8 | Control | −35,369.05 ± 5,180.61 | 0.000*** |
| | 8 | Test | −72,941.62 ± 5,427.48 | 0.000*** |

†p-value: Independent t-test (*p < 0.05, p < 0.01, *p < 0.001)
†p-value^: Mann-Whitney test

2-4. Skin Color Brightness (L*Value)

As compared with before the product administration, at the cheek portion, in 4 weeks after the product administration, the skin color brightness was significantly increased in the test group, and in 8 weeks after the product administration, the skin color brightness was significantly increased in both the control group and the test group. At the pigmented portion, in 4 weeks and 8 weeks after the product administration, the skin color brightness (L*value) was significantly increased in both the control group and the test group ($p<0.05$). In comparison between the groups, in 4 weeks and 8 weeks after the product administration at the cheek portion and in 8 weeks after the product administration at the pigmented portion, as compared with the control group, in the test group, the skin color brightness (L*value) was significantly increased ($p<0.05$) (Table 9).

TABLE 9

Comparison of Skin color brightness (L*value) between groups depending on time

| Site | Weeks | Group | ΔMean difference ± Std. Error (L*value) | p-value† |
|---|---|---|---|---|
| Face (cheek) | 4 weeks | Control group | 0.25 ± 0.12 | 0.007**^ |
| | | Test group | 0.81 ± 0.32 | |
| | 8 weeks | Control group | 0.48 ± 0.15 | 0.000***^ |
| | | Test group | 2.20 ± 0.29 | |
| Dark spot | 4 weeks | Control group | 0.97 ± 0.26 | 0.215^ |
| | | Test group | 1.15 ± 0.18 | |
| | 8 weeks | Control group | 1.60 ± 0.30 | 0.004** |
| | | Test group | 2.79 ± 0.26 | |

†p-value: Independent t-test (*p < 0.05, p < 0.01, *p < 0.001 Significant difference between two groups)
†p-value^: Mann-Whitney test

2-5. Blood Analysis

As the analysis result, as compared with before the product administration, in 8 weeks after the product administration, in the control group, there was a significant difference in T. Protein, Albumin, and Creatinine items and in the test group, there was a significant difference in T. Protein, Creatinine, and Pulse items, but an average value of parameters was in a normal range ($p<0.05$). In comparison between the groups, in 8 weeks after the product administration, there was no significant difference between the two groups in all parameters (Table 10).

TABLE 10

Result of blood analysis depending on types of items

| Items | Groups | ΔMean difference ± Std. Error (L*value) | p-value† |
|---|---|---|---|
| T. Protein | Control group | −0.25 ± 0.06 | 0.743 |
| T. Protein | Test group | −0.28 ± 0.07 | 0.743 |
| Albumin | Control group | −0.10 ± 0.03 | 0.224 |
| Albumin | Test group | −0.02 ± 0.05 | 0.224 |
| T. Bil | Control group | −0.06 ± 0.04 | 0.599 |
| T. Bil | Test group | −0.10 ± 0.06 | 0.599 |
| SGOT | Control group | 0.10 ± 1.71 | 0.743^ |
| SGOT | Test group | 0.57 ± 0.84 | 0.743^ |
| SGPT | Control group | 2.45 ± 1.50 | 0.617 |
| SGPT | Test group | 1.48 ± 1.23 | 0.617 |
| T. Chol | Control group | −1.25 ± 3.14 | 0.607 |
| T. Chol | Test group | −3.57 ± 3.19 | 0.607 |
| Triglyceride | Control group | 1.70 ± 15.20 | 0.754^ |
| Triglyceride | Test group | −13.24 ± 8.07 | 0.754^ |
| Blood glucose level (Before eating) | Control group | −2.70 ± 2.12 | 0.530 |
| Blood glucose level (Before eating) | Test group | −0.62 ± 2.49 | 0.530 |
| BUN (Urea nitrogen) | Control group | 0.59 ± 0.66 | 0.879 |
| BUN (Urea nitrogen) | Test group | 0.44 ± 0.69 | 0.879 |
| Creatinine | Control group | 0.06 ± 0.02 | 0.758^ |
| Creatinine | Test group | 0.08 ± 0.02 | 0.758^ |
| Hemoglobin | Control group | 0.10 ± 0.11 | 0.875^ |
| Hemoglobin | Test group | 0.03 ± 0.16 | 0.875^ |
| Systolic blood pressure | Control group | 1.35 ± 2.37 | 0.343 |
| Systolic blood pressure | Test group | 4.76 ± 2.64 | 0.343 |
| Diastolic pressure | Control group | −1.30 ± 1.12 | 0.117 |
| Diastolic pressure | Test group | 2.19 ± 1.83 | 0.117 |

TABLE 10-continued

Result of blood analysis depending on types of items

| Items | Groups | ΔMean difference ± Std. Error (L*value) | p-value† |
|---|---|---|---|
| Pulse | Control group | 2.80 ± 1.86 | 0.290^ |
| Pulse | Test group | 5.38 ± 1.80 | 0.290^ |

†p-value: Independent t-test (*p < 0.05, p < 0.01, *p < 0.001 Significant difference between two groups)
†p-value^: Mann-Whitney test 2-6. Diet Survey and Weight As the analysis result, as compared with before the product administration, in 8 weeks after the product administration, in the test group, the weight was significantly increased, but in 4 weeks and 8 weeks after the product administration, there was no significant difference in diet survey, weight, and BMI index (p<0.05), In comparison between the groups, in 4 weeks and 8 weeks after the product administration, in both the control group and the test group, there was no significant difference in diet survey, weight, and BMI index (p<0.05) (Table 11).

TABLE 11

Diet survey and changes in weight between groups depending on time (n = 41)

| Items | Weeks | Groups | ΔMean difference ± Std. Error (L*value) | p-value† |
|---|---|---|---|---|
| Diet survey | 4 weeks | Control group | 0.01 ± 0.02 | 0.213^ |
| Diet survey | 4 weeks | Test group | −0.01 ± 0.03 | 0.213^ |
| Diet survey | 8 weeks | Control group | 0.03 ± 0.02 | 0.168^ |
| Diet survey | 8 weeks | Test group | −0.01 ± 0.02 | 0.168^ |
| weight | 4 weeks | Control group | 0.31 ± 0.15 | 0.794 |
| weight | 4 weeks | Test group | 0.24 ± 0.20 | 0.794 |
| weight | 8 weeks | Control group | 0.55 ± 0.27 | 0.676^ |
| weight | 8 weeks | Test group | 0.67 ± 0.25 | 0.676^ |
| BMI index | 4 weeks | Control group | 0.05 ± 0.07 | 0.574 |
| BMI index | 4 weeks | Test group | 0.11 ± 0.09 | 0.574 |
| BMI index | 8 weeks | Control group | 0.22 ± 0.12 | 0.947 |
| BMI index | 8 weeks | Test group | 0.21 ± 0.11 | 0.947 |

†p-value: Independent t-test (*p < 0.05, p < 0.01, *p < 0.001 Significant difference between two groups)
†p-value^: Mann-Whitney test 3. Questionnaire Evaluation Result 3-1. Questionnaire Evaluation Result on Efficacy In items of 'moisturizing skin', 'softening', 'reduced pulling', 'reduced dead skin', and 'healthy skin', in 4 weeks and 8 weeks after the product administration, 60% and 70% or more of the subjects answered that the items were positively improved in both the control product and the test product. In particular, in 4 weeks after the product administration, items of 'reduced pulling' and 'ordered skin texture' were improved 10% or more in the test product as compared with the control group (Table 12).

TABLE 12

Questionnaire evaluation result on efficacy depending on time (n = 41)

| Items | Week | Control group (n = 20) Positive responses (N) | Control group (n = 20) Satisfaction (%) | Test group (n = 21) Positive responses (N) | Test group (n = 21) Satisfaction (%) |
|---|---|---|---|---|---|
| Level of improving in skin moisturizing† | 4 W | 9 | 45.00% | 8 | 38.10 |
| | 8 W | 13 | 65.00% | 11 | 52.38 |
| Level of improving in skin color† | 4 W | 8 | 40.00% | 8 | 38.10 |
| | 8 W | 11 | 55.00% | 9 | 42.86 |
| 1. moisturizing skin | 4 W | 14 | 70.00% | 14 | 66.67 |
| | 8 W | 16 | 80.00% | 16 | 76.19 |
| 2. softening | 4 W | 17 | 85.00% | 15 | 71.43 |
| | 8 W | 18 | 90.00% | 18 | 85.71 |
| 3. reduced pulling | 4 W | 13 | 65.00% | 17 | 80.95 |
| | 8 W | 15 | 75.00% | 16 | 76.19 |
| 4. reduced dead skin | 4 W | 12 | 60.00% | 14 | 66.67 |
| | 8 W | 16 | 80.00% | 17 | 80.95 |
| 5. ordered skin texture | 4 W | 12 | 60.00% | 15 | 71.43 |
| | 8 W | 16 | 80.00% | 13 | 61.90 |
| 6. brightened skin | 4 W | 12 | 60.00% | 12 | 57.14 |
| | 8 W | 14 | 70.00% | 16 | 76.19 |
| 7. healthy skin | 4 W | 15 | 75.00% | 13 | 61.90 |
| | 8 W | 16 | 80.00% | 17 | 80.95 |

Criteria for questionnaire†: 0, No change/1, feels small change but do not know the change/2, feels a little improvement/3, feels improved/4, very much improved
Examiners answered positively (%): 2~4
Criteria for questionnaire 1. Not at all/2. No/3. It seems no/4. It seems likely/5. Likely/6. Very likely.
Examiners answered positively (%): 4~6

3-2. Questionnaire Evaluation Result on Product Usability

In all items except for 'chewing feeling', 70% or more of the subjects positively answered in the control product and the test product. Particularly, in items of 'taste of product' and 'overall product satisfaction', 100% of the subjects answered that the items were satisfied in the test group (Table 13).

TABLE 13

Questionnaire on product usability after using product

| Items | Control group (n = 20) Positive responses (N) | Control group (n = 20) Satisfaction (%) | Test group (n = 21) Positive responses (N) | Test group (n = 21) Satisfaction (%) |
|---|---|---|---|---|
| 1. How about the color of the product? | 16 | 80.00 | 20 | 95.24% |
| 2. How about the flavor of the product? | 18 | 90.00 | 19 | 90.48% |
| 3. How about taste of the product? | 19 | 95.00 | 21 | 100.00% |
| 4. How about the form of the product? | 14 | 70.00 | 17 | 80.95% |
| 5. How about feeling on chewing the product? | 14 | 70.00 | 11 | 52.38% |
| 6. Are you satisfied with the product overall? | 18 | 90.00 | 21 | 100.00% |
| 7. Do you have an intention to purchase of the product, if the product is released? | 15 | 75.00 | 15 | 71.43% |

Criteria for questionnaire 1. Not good at all/2. Not good/3. Normal/4. It seems good/5. Very good.
Examiners answered positively (%): 4~5

4. Safety Evaluation Result

For the present test period, no adverse reactions to skin and whole body systemic symptoms were observed in all subjects.

As the above result, it is determined that the present test product helps in improvement of skin moisture, dead skin quantity, transepidermal water loss (TEWL) and skin color.

Example 9: Preparation of Cosmetics Including *Lactobacillus Plantarum* K8 Lysate (*Lactobacillus Plantarum* K8-LTA) and Human Body Application Test Clinical Trial Result Three types of cosmetics including *Lactobacillus plantarum* K8-LTA were prepared and experiments for evaluating efficacy of improving skin moisturizing, skin color, skin elasticity, eye wrinkles and dermis density were performed.

Tests in wrinkles and pigmentation were conducted by targeting 32 female subjects aged 35 to 50. While test products (Table 14) were continuously used for 8 weeks of a test period, at time points of before using the products, 4 weeks after using the products, and 8 weeks after using the products, visual evaluation (eye wrinkles, skin color) and device measurement (skin moisturizing, skin color, skin elasticity, eye wrinkles, and dermal density) were performed. Left/right measurement portions were defined by Block randomization (A: moisturizing and dermal density of the left cheek, measurement of skin color, elasticity, measurement of eye wrinkles of the right cheek/B: moisturizing and dermal density of the right cheek, measurement of skin color, elasticity, and measurement of eye wrinkles of the left cheek), and safety and questionnaire evaluation were performed in 4 weeks and 8 weeks after using the products.

TABLE 14

| Information on Cosmetics | |
| --- | --- |
| Name of cosmetics | k-lac Bio Essential Intensive Toner |
| | k-lac Bio Essential Ample Essence |
| | k-lac Bio Essential Intensive Lifting Cream |
| Type of cosmetics | Toner: colorless and solubilized type |
| | Essence: white and cream type |
| | Cream: white and cream type |
| Duration of using cosmetics | For 8 weeks |
| Method of using cosmetics | apply the appropriate amount of face with an order of toner - essence - cream in the morning and evening, after washing face |
| Used part of product | Whole face |

The subjects participated in device measurement after stabilization for at least 20 minutes after cleansing in a space where there are no movement of air and direct sunlight and constant temperature and humidity conditions (22±2° C. and 50±5%) are maintained.

1. Visual Evaluation 1-1. Visual Evaluation Analysis of Eye Wrinkles for Each Time As compared with before using the test products, in 4 weeks and 8 weeks after using the products, the wrinkles were significantly improved (P<0.05), and the maximum variation of wrinkles improvement was a decrease (improvement) rate of 5.50% (see Table 15).

TABLE 15

Changes in eye wrinkles before and after using the test products depending on time (n = 32)

| Time of measurement | Mean(Grade) | S.D | p-value† | decrease or improvement rate [1] (%) |
| --- | --- | --- | --- | --- |
| 0 W | 4.73 | 0.85 | — | — |
| 4 W | 4.58 | 0.77 | 0.005** | ▼ 3.17 |
| 8 W | 4.47 | 0.78 | 0.000*** | ▼ 5.50 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value 1-2. Visual Evaluation Analysis of Skin Color for Each Time As compared with before using the test products, in 4 weeks and 8 weeks after using the products, the skin color was significantly improved (P<0.05), and the maximum variation of skin color improvement was a decrease (improvement) rate of 9.04% (see Table 16).

TABLE 16

Changes in skin color before and after using the test products depending on time (n = 32)

| Time of measurement | Mean(Grade) | S.D | p-value† | decrease or improvement rate[1] (%) |
| --- | --- | --- | --- | --- |
| 0 W | 5.09 | 1.26 | — | — |
| 4 W | 4.77 | 1.39 | 0.000*** | ▼ 6.29 |
| 8 W | 4.63 | 1.36 | 0.000*** | ▼ 9.04 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value 2. Device Measurement 2-1. Measurement of Moisture As compared with before using the test products, in 4 weeks and 8 weeks after using the products, the moisture was statistically significantly increased (improved) (P<0.05), and the maximum variation of moisture improvement was an increase (improvement) rate of 42.97% (see Table 17).

TABLE 17

Changes in skin moisture before and after using the test products depending on time (n = 32)

| Time of measurement | Mean(Grade) | S.D | p-value† | decrease or improvement rate[1] (%) |
| --- | --- | --- | --- | --- |
| 0 W | 27.51 | 6.80 | — | — |
| 4 W | 34.02 | 5.54 | 0.000*** | ▲ 23.66 |
| 8 W | 39.33 | 6.15 | 0.000*** | ▲ 42.97 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value 2-2. Measurement of Skin Color Brightness (L*Value)

As compared with before using the test products, in 4 weeks and 8 weeks after using the products, the skin color brightness degree at the cheek portion was statistically significantly increased (improved) (P<0.05), and in 8 weeks after using the products, the brightness degree at the pigmented portion was statistically significantly increased (improved) (P<0.05). The maximum variation of skin color brightness improvement was an increase (improvement) rate of 1.59% at the cheek portion and 1.25% at the pigmented portion.

TABLE 18

Changes in skin color before and after using the test products depending on time (n = 32)

| Site | Time of measurement | Mean(Grade) | S.D | p-value† | decrease or improvement rate [1] (%) |
|---|---|---|---|---|---|
| Cheek | 0 W | 62.14 | 3.19 | — | — |
| | 4 W | 62.78 | 3.07 | 0.005** | ▲ 1.03 |
| | 8 W | 63.13 | 2.90 | 0.000*** | ▲ 1.59 |
| Pigmentation | 0 W | 59.09 | 3.27 | — | — |
| | 4 W | 59.34 | 3.23 | 0.155 | ▲ 0.42 |
| | 8 W | 59.83 | 3.06 | 0.000*** | ▲ 1.25 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value 2-3. Measurement of Skin Elasticity (Moire Topography System)

As compared with before using the test products, in 4 weeks and 8 weeks after using the products, the total distance and an average angle of the contour lines were statistically significantly decreased (improved) (P<0.05).

The maximum decrease rate of the entire length of the contour line was 9.64% and the maximum decrease rate of the angle was 14.70% (Table 19)

TABLE 19

Analysis result of skin elasticity before and after using the test products depending on time (n = 32)

| Category | Time of measurement | Mean | S.D | p-value† | decrease or improvement rate [1] (%) |
|---|---|---|---|---|---|
| Distance (pixel) | 0 W | 270.31 | 61.76 | — | — |
| Distance (pixel) | 4 W | 253.81 | 63.78 | 0.000*** | ▼ 6.10 |
| Distance (pixel) | 8 W | 244.25 | 54.87 | 0.000*** | ▼ 9.64 |
| Angle (°) | 0 W | 26.74 | 5.78 | — | — |
| Angle (°) | 4 W | 24.68 | 5.81 | 0.000*** | ▼ 7.70 |
| Angle (°) | 8 W | 22.81 | 5.18 | 0.000*** | ▼ 14.70 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value 2-4. Measurement of Eye Wrinkles As compared with before using the test products, in 4 weeks after using the products, a mean depth of wrinkles and a max wrinkle depth were statistically significantly decreased (improved) and in 8 weeks after using the products, the max wrinkle depth was statistically significantly decreased (improved) (p<0.05).

The maximum decrease rate of the 'mean depth of wrinkles' was 8.36% and the maximum decrease rate of the 'maximum depth of the wrinkles' was 26.17% (Table 20).

TABLE 20

Analysis result of eye wrinkle before and after using the test products depending on time (n = 32)

| Category | Time of measurement | Mean | S.D | p-value† | decrease or improvement rate [1] (%) |
|---|---|---|---|---|---|
| Total wrinkle area (mm²) | 0 W | 34.82 | 6.81 | — | — |
| | 4 W | 34.68 | 8.32 | 0.903 | ▼ 0.40 |
| | 8 W | 33.83 | 7.84 | 0.377 | ▼ 2.84 |
| Wrinkle number (N) | 0 W | 65.43 | 35.01 | — | — |
| | 4 W | 65.25 | 34.97 | 0.976 | ▼ 0.28 |
| | 8 W | 65.34 | 31.97 | 0.986 | ▼ 0.14 |
| Average length of wrinkles (mm) | 0 W | 0.91 | 0.24 | — | — |
| | 4 W | 0.91 | 0.32 | 0.883 | 0.00 |
| | 8 W | 0.93 | 0.31 | 0.721 | ▲ 2.20 |
| Average depth of wrinkles (μm) | 0 W | 80.86 | 14.67 | — | — |
| | 4 W | 74.10 | 15.49 | 0.009** | ▼ 8.36 |
| | 8 W | 78.97 | 16.95 | 0.377 | ▼ 2.34 |
| Maximum wrinkle depth (μm) | 0 W | 407.69 | 151.83 | — | — |
| | 4 W | 301.01 | 96.64 | 0.000*** | ▼ 26.17 |
| | 8 W | 330.20 | 104.30 | 0.005** | ▼ 19.01 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value

2-5. Measurement of Skin Dermal Density

As compared with before using the test products, in 8 weeks after using the products, the thickness of dermis was statistically significantly increased (improved) and in 4 weeks and 8 weeks after using the products, the density of dermis was statistically significantly increased (improved) ($p<0.05$).

The maximum increase rate of the dermis thickness was 10.16% and the maximum increase rate of the dermis density was 13.55% (Table 21).

TABLE 21

Analysis result of skin dermal density before and after using the test products depending on time (n = 32)

| Category | Time of measurement | Mean | S.D | p-value† | decrease or improvement rate [1] (%) |
|---|---|---|---|---|---|
| Distance (mm) | 0 W | 1.28 | 0.16 | — | — |
| Distance (mm) | 4 W | 1.29 | 0.15 | 0.569 | ▲ 0.78 |
| Distance (mm) | 8 W | 1.41 | 0.16 | 0.000*** | ▲ 10.16 |
| Intensity (%) | 0 W | 15.28 | 1.92 | — | — |
| Intensity (%) | 4 W | 16.88 | 1.66 | 0.000*** | ▲ 10.47 |
| Intensity (%) | 8 W | 17.35 | 1.42 | 0.000*** | ▲ 13.55 |

†p-value: Paired t-test (*p < 0.05, p < 0.01, *p < 0.001, Significant difference compared to before using the product)
[1] decrease or improvement rate: $(W_x - W_0)/W_0 \times 100$, calculated by mean value

3. Questionnaire Evaluation

3-1. Questionnaire Evaluation of Efficacy

In 4 weeks and 8 weeks after using the products, the evaluation result on the efficacy of the products answered by the subjects through questionnaire was as follows (Table 22).

TABLE 22

Results of questionnaire evaluation in effects

| | | | |
|---|---|---|---|
| Level of improving in skin color† | 4 W | 3 | 9.38 |
| | 8 W | 17 | 53.13 |
| Level of improving in skin wrinkles† | 4 W | 3 | 9.38 |
| | 8 W | 9 | 28.13 |
| 1. moisturizing skin | 4 W | 22 | 68.75 |
| | 8 W | 29 | 90.63 |
| 2. softening | 4 W | 27 | 84.38 |
| | 8 W | 32 | 100.00 |
| 3. ordered skin texture | 4 W | 25 | 78.13 |
| | 8 W | 32 | 100.00 |
| 4. brightened skin | 4 W | 22 | 68.75 |
| | 8 W | 30 | 93.75 |
| 5. clear skin | 4 W | 22 | 68.75 |
| | 8 W | 30 | 93.75 |
| 6. Reduced skin sagging | 4 W | 19 | 59.38 |
| | 8 W | 25 | 78.13 |
| 7. healthy skin | 4 W | 23 | 71.88 |
| | 8 W | 32 | 100.00 |

Criteria for questionnaire†: 0, No change/1, feels small change but do not know the change/2, feels a little improvement/3, feels improved/4, very much improved.
Examiners answered positively (%): 3~4
Criteria for questionnaire 1. Not at all/2. No/3. It seems no/4. It seems likely/5. Likely/6. Very likely.
Examiners answered positively (%): 4~6

3-2. Questionnaire Evaluation of Product Usability

In 8 weeks after using the products, the evaluation result on the final usability of the products answered by the subjects through questionnaire was as follows (Table 23).

TABLE 23

Questionnaire on product usability

| | Toner | | Essence | | cream | |
|---|---|---|---|---|---|---|
| Items | Positive Response (N) | Satisfaction (%) | Positive Response (N) | Satisfaction (%) | Positive Response (N) | Satisfaction (%) |
| 1. How about the color of the product? | 23 | 71.88 | 26 | 81.25 | 28 | 87.50 |
| 2. How about the flavor of the product? | 19 | 59.38 | 18 | 56.25 | 17 | 53.13 |
| 3. How about the viscosity of the product? | 18 | 56.25 | 23 | 71.88 | 20 | 62.50 |
| 4. How about the adsorption rate of the product? | 21 | 65.63 | 24 | 75.00 | 24 | 75.00 |
| 5. How about the level of skin moist after adsorption of the product? | 18 | 56.25 | 30 | 93.75 | 26 | 81.25 |
| 6. Are you satisfied with the product overall? | 28 | 87.50 | 29 | 90.63 | 27 | 84.38 |
| 7. Do you have an intention to purchase of the product, if have an opportunity? | 24 | 75.00 | 29 | 90.63 | 25 | 78.13 |

4. Evaluation of Safety

In 4 weeks and 8 weeks after using the products, the evaluation of subjective and objective stimuli was performed by a tester by observing and questioning the subject's skin condition.

For the present test period, no adverse reactions to skin were observed in all subjects (Table 24).

TABLE 24

Evaluation of safety: adverse reactions to skin (n = 32)

| Time of measurement | Symptoms | Subjective feeling of stimulation | | | | | | | Objective feeling of stimulation | | | |
|---|---|---|---|---|---|---|---|---|---|---|---|---|
| | | itch | Stinging pain | irritating | burning | tingling | stiffness | pulling | erythema | edema | dead skin | Pimple/rash |
| 4 W | Weak | 0 | 0 | 0 | 0 | 0 | 0 | 0 | 0 | 0 | 0 | 0 |
| 4 W | Moderate | 0 | 0 | 0 | 0 | 0 | 0 | 0 | 0 | 0 | 0 | 0 |
| 4 W | Severe | 0 | 0 | 0 | 0 | 0 | 0 | 0 | 0 | 0 | 0 | 0 |
| 8 W | Weak | 0 | 0 | 0 | 0 | 0 | 0 | 0 | 0 | 0 | 0 | 0 |
| 8 W | Moderate | 0 | 0 | 0 | 0 | 0 | 0 | 0 | 0 | 0 | 0 | 0 |
| 8 W | Severe | 0 | 0 | 0 | 0 | 0 | 0 | 0 | 0 | 0 | 0 | 0 |
| Number of adverse reactions (Total) | | 0 | 0 | 0 | 0 | 0 | 0 | 0 | 0 | 0 | 0 | 0 |

It is determined that the present test products (three cosmetics) helps in the improvement of skin moisturizing, skin color, skin elasticity, skin color, eye wrinkles, and dermis density.

PREPARATION EXAMPLES

Preparation Example 1: Preparation of Candy Containing *Lactobacillus Plantarum* K8 Lysate (*Lactobacillus Plantarum* K8-LTA)

A candy containing vegetable *Lactobacillus plantarum* K8 lysates was prepared. Raw materials used in the preparation of the candy included purified glucose, *Lactobacillus plantarum* K8 lysates 2.1%, xylitol 2%, vitamin C, blueberry extract powder, anhydrous citric acid, DL-malic acid, synthetic flavoring agents (blueberry flavor and raspberry flavor), enzyme-treated stevia, and magnesium stearate and were listed in Table 5. Next, an experiment for determining whether aglycone isoflavone was included in the prepared candy was performed. Three test candies having different lot numbers and three control candies (showing ingredients in Table 25) were selected, grinded by using a mortar, and then suspended in sterile distilled water. The suspended candy samples were crushed by using a sonicator and then extracted by using ethanol. An ethanol layer was mixed with methanol and then the LC/MS-MS analysis was performed. As a result, daidzein and genistein as aglycone isoflavones were detected from the test candies, but were not detected in the control candies (Table 26).

TABLE 25

Comparison of ingredients in candies

| | Sample | Control |
|---|---|---|
| Title | Plant Probiotic-contained candy | Plant Probiotic free candy |
| Label | Sample | Control |
| Composition | Glucose, *L. plantarum* K8-LTA cell lysates 2.1%, Xylitol 2%, Vitamin C, Blueberry concentrate powder, Citric acid anhydrous, DL-malic acid, combined congener (Blueberry flavor, raspberry flavor), Enzymatically Modified Stevia Glucosyl Stevia, Magnesium Stearate | Glucose, Xylitol 2%, Vitamin C, Blueberry concentrate powder, Citric acid anhydrous, DL-malic acid, combined congener (Blueberry flavor, raspberry flavor), Enzymatically Modified Stevia Glucosyl Stevia, Magnesium Stearate |
| Property | Mauve candy | Mauve candy |
| Package | White airtight container | White airtight container |
| Storage | Room temperature | Room temperature |

TABLE 26

Result of measuring aglycone isoflavone in candies

| | Daidzein† | Genistein† |
|---|---|---|
| Control Candy | 0 | 0 |
| Sample Candy | 0.103 ± 0.064 | 0.093 ± 0.021 |

†Aglycone isoflavone contents in candies: Mean ± S.D. (ng/ml)

Preparation Example 2

Preparation of Intestinal Regulation Agent of Lactic Acid Bacteria Containing Aglycone or Hydrolyzed Glycoside

*Lactobacillus plantarum* K8 was mass-incubated in an MRS medium added with various glycosides such as saponin or isoflavone glycoside according to a method known in the art to prepare lactic acid bacteria raw powder. A small amount of calcium and vitamin D was mixed with the prepared *Lactobacillus plantarum* K8 raw powder to prepare an intestinal regulation product. The detailed compositions were described in Table 27 below. In order to enhance an intestinal regulation effect, a small amount of other lactic acid bacteria raw powder having an intestinal regulation effect, for example, bifidus bacteria raw powder known to exist in the large intestine may be added.

TABLE 27

Components of intestinal regulation agent including *Lactobacillus plantarum* K8

| Components | 1 pack (wt %) |
|---|---|
| *Lactobacillus plantarum* K8 | 70 |
| Vitamin D | 15 |
| Calcium | 15 |
| Total | 100 |

Preparation Example 3: Preparation of Raw Food Including Lactic Acid Bacteria Containing Aglycone or Hydrolyzed Glycoside Various kinds of cereal powder, seaweed powder, fruit and vegetable powder, mushroom powder and the aglycone lactic acid bacteria raw powder of the present disclosure were mixed with soybean embryo fermentation powder to prepare raw food products. The detailed compositions were described in Table 28 below.

TABLE 28 raw food including *Lactobacillus plantarum* K8

| Components | 1 pack (wt %) |
|---|---|
| Soybean germ fermentation powder | 25 |
| Brown rice powder | 10 |
| Barley powder | 5 |
| Corn powder | 3 |
| Soybean powder | 3 |
| Adlay powder | 3 |
| Sesame powder | 3 |
| Red bean powder | 3 |
| Weed powder | 5 |
| Seaweed powder | 8 |
| Kelp powder | 12 |
| Kale powder | 5 |
| *Aloe* powder | 3 |
| Carrot powder | 2 |
| Shiitake mushroom powder | 4 |
| *Ganoderma lucidum* powder | 4 |
| *Lactobacillus plantarum* K8 | 2 |
| Total | 100 |

Preparation Example 4: Preparation of Fermented Milk Including Lactic Acid Bacteria Containing Aglycone or Hydrolyzed Glycoside Skim milk or crude milk was mixed with a culture solution 1% in which *Lactobacillus plantarum* K8 of the present disclosure was pre-incubated and fermented for 6 to 8 hrs at 40° C. to prepare fermented milk. The detailed compositions were described in Table 29 below. When fermenting the skim milk or the crude milk, in order to shorten a fermentation time and improve the flavor of the fermented milk, *streptococcus thermophilus* or *Lactobacillus acidophilus*, which is commercially available, may be used together.

TABLE 29 components of fermented milk including lactic acid bacteria containing aglycone or hydrolyzed glycoside

| Components | 1 pack (wt %) |
|---|---|
| Nonfat dry milk | 95 |
| Oligosaccharide | 4 |
| Lactic acid bacteria containing aglycone or hydrolyzed glycoside - | 1 |
| Total | 100 |

Preparation Example 6: Preparation of Fermented Soybean Liquid Using *Lactobacillus Plantarum* K8

A soybean liquid was mixed with a culture solution 1% in which *Lactobacillus plantarum* K8 of the present disclosure was pre-incubated and fermented for 6 to 8 hrs at 40° C. to prepare a fermented soybean liquid. The detailed compositions were described in Table 30 below. When fermenting the soybean liquid, in order to shorten a fermentation time and improve the flavor of the fermented milk, *streptococcus thermophilus* or *Lactobacillus acidophilus*, which is commercially available, may be used together.

TABLE 30 components of fermented soybean liquid containing *Lactobacillus plantarum* K8

| Components | 1 pack (wt %) |
|---|---|
| Soybean liquid | 90 |
| Oligosaccharide | 9 |
| *Lactobacillus plantarum* K8 | 1 |
| Total | 100 |

Preparation Example 7: Preparation of Red Ginseng Lactic Acid Bacteria

*Lactobacillus plantarum* K8 of the present disclosure was incubated in 100 L of a minimal medium including red ginseng extracts 0.1% for 12 hrs and then the cells were collected. The collected cells were washed with water and then lyophilized and included in a microcapsule to prepare red ginseng lactic acid bacteria. The microcapsule may improve adhesion and cohesion by considering an addition condition of a plasticizer, a type of plasticizer, and surface tension of the capsules when a matrix is formed by a wall material and a coagulating liquid. Because the outside and the inside of the capsule make hard gelation, the survival rate of the lactic acid bacteria in stomach acid is increased and lactic acid bacteria capsules having high activity in the intestines are made. As a primary coating solution, Na alginate 1.8%, glycerol 10%, xanthan gum 0.32%, Tween 20 0.05%, and MRS 5% were used, as a hardening solution, $CaCl_2$ 0.5 M and Tween 80 0.5% were used, and as a secondary coating solution, chitosan 1.5% and lactic acid 1.5% were used. Through the experiment, it was confirmed that the red ginseng lactic acid bacteria capsules produced by the condition were dissolved in the artificial intestinal fluid at pH 7.4. Further, for an anti-acid test, the ginseng lactic acid bacteria capsules reacted in the artificial stomach liquid at pH 1.4 up to 180 minutes at time intervals and then released from the artificial intestinal liquid and the viable cell count was measured, and as a result, the survival rate in the artificial stomach liquid was about 95%.

According to the preparing method of the present disclosure, through the microorganism having ability of converting the glycoside into the aglycone or hydrolyzed glycoside and ability of accumulating the converted aglycone or hydrolyzed glycoside in the cells, a microorganism capable of preparing aglycones or hydrolyzed glycoside in a high concentration may be provided. Further, microorganism viable cells or lysates thereof containing the aglycone or hydrolyzed glycoside produced by the preparing method of the present disclosure are prepared and may be variously used for preparation of antioxidant compositions, intestinal regulation agents, probiotic compositions, feed additives, food additives, raw materials for cosmetics and other fermented products.

Although the specific part of the present disclosure has been described in detail, it is obvious to those skilled in the art that such a specific description is just a preferred embodiment and the scope of the present disclosure is not limited. Thus, the substantial scope of the present disclosure will be defined by the appended claims and equivalents thereof.

What is claimed is:

1. A method of preparing a microorganism preparation showing a high body absorption rate of a converted ginsenoside, in which the converted ginsenoside is accumulated in cells, comprising accumulating the converted ginsenoside in the microorganism by incubating the microorganism expressing β-glycosidase in a medium containing ginseng extracts, wherein a concentration of the converted ginsenoside accumulated in the cells of the microorganism is more than 2 times higher than that of the converted ginsenoside in the medium.

2. The method according to claim 1, wherein the converted ginsenoside is selected from the group consisting of rg3, rc, and f2, and the ginseng extracts comprise one or more of a ginsenoside selected from the group consisting of rg1 and rb 1.

3. The method according to claim 1, wherein the microorganism expressing β-glycosidase is one or more selected from the group consisting of lactic acid bacteria, bifidus, yeast, corynebacterium, aspergillus and clostridium.

4. The method according to claim 3, wherein the lactic acid bacteria is one or more selected from the group consisting of *L. plantarum, L. sakei, L. rhamnosus GG, L. delbrueckii, L. acidophilus, L. johnsonii, L. casei* and *L. gasser*.

5. The method according to claim 3, wherein the lactic acid bacteria is *Lactobacillus plantarum* K8 (accession number: KCTC 10887BP).

6. The method according to claim 1, wherein the microorganism producing the β-glycosidase is one or more selected from the group consisting of generally recognized as safe (GRAS) microorganisms, bifidus, yeast, *Bacillus licheniformis, S. thermophilus, L. casei, Streptomyces* sp. *Bifidobacteria, Lactobacillus delbrueckii* Rh2, *Sporosarcina* sp., *Saccharomyces cerevisiae, Pyrococcus furiosus, Lactobacillus plantarum, Aspergillus ochraceus, Aactobacillus delbrueckii* Rh2, *Pseudomonas* sp., *Aspergillus niger, Pseudomonas fluorescens, Bifidobacterium adolescentis, Aspergillus sojae, Cunninghamella blakesleeana, Cifidobacteria and Lactobacillus, Lactic acid bacteria, Bifidobacterium pseudocatenulatum, Penicillium melinii, Eubacterium ramulus, Clostridium orbiscindens, Aspergillus awamori, Lactobacillus brevis, Aspergillus parasiticus speare* BGB, *Aspergillus aculeatus*, and *Aspergillus niger*.

7. The method according to claim 1, wherein the incubating the microorganism comprises steps of static culture for microbial activation, shaking culture, and feeding culture in sequence.

8. The method according to claim 7, wherein the static culture is performed for 12 hrs at 37° C.

9. The method according to claim 7, wherein the shaking culture is performed under a condition of 6 rpm for 12 hrs at 37° C.

10. The method according to claim 1, wherein the incubating further comprises inoculating and then incubating the microorganism in a medium, is followed by transferring to a minimal medium comprising a glycoside and then culturing the microorganism additionally for 1 to 36 hrs.

* * * * *

UNITED STATES PATENT AND TRADEMARK OFFICE
CERTIFICATE OF CORRECTION

PATENT NO.        : 10,676,708 B2
APPLICATION NO.   : 15/515918
DATED             : June 9, 2020
INVENTOR(S)       : Dae Kyun Chung et al.

It is certified that error appears in the above-identified patent and that said Letters Patent is hereby corrected as shown below:

In the Claims

Column 30, Line 7: "gasser" should be -- gasseri --

Signed and Sealed this
Twenty-first Day of July, 2020

Andrei Iancu
*Director of the United States Patent and Trademark Office*